United States Patent [19]

Noda et al.

[11] E Patent Number: Re. 33,188

[45] Reissued Date of Patent: Mar. 27, 1990

[54] PEPTIDES FOR ASSAYING HUMAN PARATHYROID HORMONE

[75] Inventors: Toshiharu Noda; Kaoru Morita, both of Shizuoka; Sadami Kobari, Mishima; Nobuaki Nakagawa, Shizuoka; Susumu Watanabe, Shizuoka; Shigeo Katsuragi, Shizuoka; Kunio Ohyama, Shizuoka; Masahiko Taniuchi, Mishima, all of Japan

[73] Assignee: Toyo Jozo Kabushiki Kaisha, Shizuoka, Japan

[21] Appl. No.: 332,801

[22] Filed: Apr. 3, 1989

Related U.S. Patent Documents

Reissue of:

[64] Patent No.: 4,409,141
Issued: Oct. 11, 1983
Appl. No.: 335,401
Filed: Dec. 29, 1981

[30] Foreign Application Priority Data

| | | | |
|---|---|---|---|
| Dec. 29, 1980 | [JP] | Japan | 55-187686 |
| Apr. 16, 1981 | [JP] | Japan | 56-057691 |
| Sep. 25, 1981 | [JP] | Japan | 56-152377 |

[51] Int. Cl.[4] ..... C07K 7/10
[52] U.S. Cl. ..... 530/324; 530/399
[58] Field of Search ..... 530/324, 399

[56] References Cited

U.S. PATENT DOCUMENTS

| | | | |
|---|---|---|---|
| 3,886,132 | 5/1975 | Brewer et al. | 530/324 |
| 4,086,196 | 4/1978 | Tregear | 530/324 |

FOREIGN PATENT DOCUMENTS

| | | |
|---|---|---|
| 1008846 | 4/1977 | Canada . |
| 1413198 | 11/1975 | United Kingdom . |

OTHER PUBLICATIONS

Rosenblatt, *Endocrinalogy,* 103, No. 3, 978–984 (1978).

*Primary Examiner*—Margaret Moskowitz
*Assistant Examiner*—F. T. Moezie
*Attorney, Agent, or Firm*—Young & Thompson

[57] ABSTRACT

A peptide of the formula

R—Lys—Lys—Glu—Asp—Asn—Val—Leu—Val—Glu—Ser—His—Glu—Lys—Ser—Leu—Gly—Glu—Ala—Asp—Lys—Ala—Asp—Val—Asp—Val—Leu—Thr—Lys—Ala—Lys—Ser—Gln—OH wherein R is H, H—Tyr— or $R_1$—Pro—Arg—, $R_1$ is H, H—Tyr— or $R_2$—Ala—Gly—Ser—Gln—Arg—, and $R_2$ is H, H—Cys— or H—Tyr—, or a salt thereof, is useful for assaying human parathyroid hormone (h-PTH).

1 Claim, 1 Drawing Sheet

PEPTIDES FOR ASSAYING HUMAN PARATHYROID HORMONE

Matter enclosed in heavy brackets [ ] appears in the original patent but forms no part of this reissue specification; matter printed in italics indicates the additions made by reissue.

This invention relates to peptides for assaying human parathyroid hormone (h-PTH). More particularly this invention relates to peptides of the formula R—Lys$^{53}$—Lys—Glu$^{55}$—Asp—Asn—Val—Leu—Val$^{60}$—Glu—Ser—His—Glu—Lys$^{65}$—Ser—Les—Gly—Glu—Ala$^{70}$—Asp—Lys—Ala—Asp—Val$^{75}$—Asp—Val—Leu—Thr—Lys$^{80}$—Ala—Lys—Ser—Gln$^{84}$—OH wherein R is H, H—Tyr$^{52}$— or $R_1$—Pro$^{51}$—Arg$^{52}$—, $R_1$ is H, H—Tyr$^{50}$— or $R_2$—Ala$^{46}$—Gly$^{47}$—Ser$^{48}$—Gln$^{49}$—Arg$^{50}$—, and $R_2$ is H, H—Cys$^{45}$— or H—Tyr$^{45}$—, or a salt thereof.

Human parathyroid hormone (h-PTH) is a peptide hormone consisting of 84 amino acids, and its biological activity is revealed by the 34-amino-acid residue of its N-terminal residue [G. W. Tregear, et al., Hoppe-Seyler's Z. Physiol. Chem., 355, 415 (1974)].

We have synthesized C-terminal 32-residue h-PTH [53-84], 34-residue [51-84] and 39-residue h-PTH [46-84] and injected these peptides to sensitize rabbits, and then succeeded in obtaining the specific antibody for the C-terminal.

Labelling h-PTH with iodine 125 is known to be quite difficult in radio immunoassay (RIA). h-PTH [53-84], h-PTH [51-84] and h-PTH [46-84] do not contain tyrosine, which is easily labelled with iodine 125. On the other hand, [Tyr$^{52}$] h-PTH [52-84], [Tyr$^{50}$] h-PTH [50-84] and [Thr$^{45}$] h-PTH [45-84] can easily be labelled with a radio iostope labelling substance, and are difficult to adsorb on an immune reaction tube. Therefore, we have found that these h-PTH fragments are useful as labelled compounds for h-PTH assay due to less non-specific adsorption and accurate quantitative assay on RIA.

h-PTH [53-84], h-PTH [51-84] and h-PTH [46-84] do not contain amino acid cysteine which can be labelled with an SH-binding enzyme. However, we have found that these peptides can be quantitatively assayed, based on EIA using an antibody against the h-PTH C-terminal fragment, using a peptide of the formula $R_2$'-Ala$^{46}$—Gly—Ser—Gln—Arg—Pro$^{51}$—Arg—Lys$^{53}$—Lys—Glu$^{55}$—Asp—Asn—Val—Leu—Val$^{60}$—Glu—Ser—His—Glu—Lys$^{65}$—Ser—Leu—Gly—Glu—Ala$^{70}$—Asp—Lys—Ala—Asp—Val$^{75}$—Asp—Val—Leu—Thr—Lys$^{80}$—Ala—Lys—Ser—Gln$^{84}$—OH wherein $R_2$' is H or H—Cys$^{45}$—, from among the compounds of formula [I], i.e. h-PTH [46-84] and [Cys$^{45}$] h-PTH [45-84]. Most preferably, h-PTH or the C-terminal fragment of h-PTH can advantageously be assayed by using a specific antibody obtained by the immune reaction of [Cys$^{45}$] h-PTH [45-85] or its complex with a protein such as an immune complex of bovine serum albumin (BSA) as an antigen, and using an enzyme-labelled compound of the formula R'—Lys$^{53}$—Lys—Glu$^{55}$—Asp—Asn—Val—Leu—Val$^{60}$—Glu—Ser—His—Glu—Lys$^{65}$—Ser—Leu—Gly—Glu—Ala$^{70}$—Asp—Lys—Ala—Asp—Val$^{75}$—Asp—Val—Leu—Thr—Lys$^{80}$—Ala—Lys—Ser—Gln$^{84}$—OH wherein R' is H or $R_1$'—Pro$^{51}$—Arg$^{52}$—, $R_1$' is H or $R_2$'—Ala$^{45}$—Gly$^{47}$—Ser$^{47}$—Gln$^{49}$—Arg$^{50}$—, and $R_2$' is H or H—Cys$^{45}$—, from among the peptides of formula [I], i.e. h-PTH [53-84], h-PTH [51-84], h-PTH [46-84] and [Cys$^{45}$] h-PTH [45-84], as an enzyme-labelled compound on EIA.

The synthesis of peptide [I] of the present invention can be carried out as follows:

An amino acid and/or lower peptide is reacted by condensation in the order of the amino acid sequence of formula [I], and the protective group for the reactive group is released at the final stage of the reaction. The condensation reaction can be carried out by conventional peptide synthesis by repeating the attaching and removal of the protective groups and condensation. The protective groups for the synthesis of the starting materials or intermediates are conventional protective groups for peptide synthesis and are easily removable by hydrolysis, acid decomposition, reduction, aminolysis or hydrazinolysis.

For example, the amino group may be protected conventionally by an acyl group such as formyl, trifluoroacetyl, phthaloyl, p-toluenesulfonyl or o-nitrophenylsulfonyl group; a benzyloxycarbonyl group such as benzyloxycarbonyl, o-bromobenzyloxycarbonyl, p-bromobenzyloxycarbonyl, o- (or p-) chlorobenzyloxycarbonyl, p-nitrobenzyloxycarbonyl or p-methoxybenzyloxycarbonyl, an aliphatic oxycarbonyl group such as trichloroethyloxycarbonyl, t-amyloxycarbonyl, t-butoxycarbonyl or diisopropylmethoxycarbonyl, or an aralkyloxycarbonyl group such as 2-phenylisopropoxycarbonyl, 2-tolylisopropoxycarbonyl or 2-p-diphenylisopropoxycarbonly. These amino groups can be protected by forming enamin reacted with 1,3-diketone such as benzoylacetone or acetylacetone.

The carboxyl group can be protected by amide formation, hydrazide formation or esterification. The amide group is substituted with a 3,4-dimethoxybenzyl or bis-(p-methoxyphenyl)-methyl group. The hydrazide group is substituted with a benzyloxycarbonyl, trichloroethyloxycarbonyl, trifluoroacetyl, t-butoxycarbonyl, trityl or 2-p-diphenyl-isopropoxycarbonyl group. The ester group is substituted with an alkanol such as methanol, ethanol, t-butanol or cyanomethylalcohol; aralkanol such as benzylalcohol, p-bromobenzylalcohol, p-chlorobenzylalcohol, p-methoxybenzylalcohol, p-nitrobenzylalcohol, 2,6-dichlorobenzylalcohol, benzhydrylalcohol, benzoylmethylalcohol, p-bromobenzoylmethylalcohol or p-chlorobenzoylmethylalcohol; a phenol such as 2,4,6-trichlorophenol, 2,4,5-trichlorophenol, pentachlorophenol, p-nitrophenol or 2,4-dinitrophenol; or a thiophenol such as thiophenol or p-nitrothiophenol. The hydroxy group is serine, or tyrosine may optionally be protected by esterification or etherification. A group protected by esterification is, for example, an acetyl group; a benzoyl group, benzyloxycarbonyl or ethyloxycarbonyl. A group protected by etherification is, for example, a benzyl, tetrahydropyranyl or t-butyl group. Protection of the hydroxy group can be effected by a 2,2,2-trifluoro-1-t-butyloxycarbonylaminoethyl or 2,2,2-trifluoro-1-benzyloxycarbonylaminoethyl group. However it is not always necessary to protect these hydroxy groups.

The amino group in the guanidino group in arginine can be protected by a nitro, tosyl, benzyloxycarbonyl or methylene-2-sulfonyl group. However, it is not always necessary to protect the guanidino group.

The imino group in histidine can be protected by a benzyl, trityl, benzyloxycarboyl, tosyl, 2,2,2-trifluoro-1-benzyloxycarbonylaminoethyl group, although the imino group does not always require to be protected.

The mercapto group in cysteine can be protected by a benzyl, p-methoxybenzyl, p-nitrobenzyl, trityl, benzylthiomethyl, ethylcarbamoyl or acetamidemethyl group.

The peptide [I] is synthesized by the condensation of amino acids or lower peptides. For example, an amino acid or peptide having a protected α-amino group and an activated terminal carboxyl group is reacted with an amino acid or peptide having a free α-amino group and protected terminal carboxyl group. On the other hand, an amino acid or peptide having an activated α-amino group and protected terminal carboxyl group is reacted with amino acid or peptide having a free terminal carboxyl group and a protected α-amino group.

The carboxyl group can be activated by, for example, an acid azide, acid anhydride, acid imidazolide or active ester, such as by converting to cyanomethyl ester, thiophenylester, p-nitrophenylester, p-nitrothiophenylester, p-methanesulfonylphenylester, thiodylester, 2,4-dinitrophenylester, 2,4,5-trichlorophenylester, 2,4,6-trichlorophenylester, pentachlorophenylester, N-hydroxysuccinimide-ester, N-hydroxyphthalimido ester, 8-hydroxyquinoline ester or N-hydroxypiperidine ester, carbodiimide, N,N'-carbonyldiimidazol or an isoxazolium salt such as Woodard reagent.

The preferred condensation reactions are the carbodiimide, azide, active ester and acid anhydride methods. In the condensation reaction, racemization should carefully be avoided, and the preferred methods are the azide, the active ester method, or the Wünsch method [Z. Naturforsch, 216, 426 (1966)] or Geiger method [Chem. Ber., 103, 788 (1970)], especially using N-ethyl-N'-3-dimethylaminopropyl-carbodiimide (WSCI) as a condensation agent.

The process of the present invention is preceded by a condensation reaction in the amino acid sequence of the formula [I], and it is preferable to synthesize from the C-terminal.

Protected h-PTH [53-84] is preferably synthesized by a modified Geiger method using WSCI with condensation of the C-terminal fragment 55-84 and the N-terminal fragment 53-54. The C-terminal fragment 55-84 is preferably synthesized with the condensation of fragment 61-84 and fragment 57-60 by a modified Geiger method using WSCI, followed by condensation therewith of the 56th and 55th amino acids by the active ester method, then condensation of the fragment 51-54 by a modified Geiger method using WSCI. The fragment 61-84 is preferably synthesized with sequential condensation of the fragment 72-84 and 71st, 70th and 69th amino acids and fragment 62-68 and the 61st amino acid by the active ester method or a modified Geiger method using WSCI.

The fragment 62-68 is preferably synthesized by the azide method with the condensation of fragment 64-68 and fragment 62-63. The fragment 72-84 is preferably synthesized by a modified Geiger method using WSCI with condensation of the fragment 77-84 and the 76th, 75th and 74th amino acids and the fragment 72-73. The fragment 77-84 is preferably synthesized by a modified Geiger method using WSCI with condensation of the fragment 82-84 and fragment 77-81.

Protected h-PTH [51-84] is preferably synthesized by condensation of the C-terminal fragment 55-84 as hereinabove, and the N-terminal fragment 51-54 by a modified Geiger method using WSCI.

Protected h-PTH[46-84] is preferably synthesized by condensation of the C-terminal fragment 55-84 as hereinabove and the N-terminal fragment 46-54 by a modified Geiger method using WSCI. The N-terminal fraction 46-54 is preferably condensed by the azide method with the fragment 51-54 and the fragment 46-50.

Protected [$Tyr^{50}$] h-PTH [52-84] is preferably condensed by a modified Geiger method using WSCI with protected h-PTH [53-84] as hereinabove and the 52nd tyrosine.

Protected [$Tyr^{50}$] h-PTH [50-80] is preferably synthesized by condensation of protected h-PTH [50-84] as hereinbefore and the 50th tyrosine by a modified Geiger method using WSCI.

Protected [$Tyr^{45}$] h-PTH [45-84] and protected [$Cys^{45}$] h-PTH [45-84] are preferably synthesized by condensation of protected h-PTH [46-84] as hereinbefore and the corresponding 45th amino acid by a modified Geiger method using WSCI.

In the peptide synthesis set forth hereinabove, the C-terminal carboxyl group need not always be protected. For example, in the condensation reaction by the azide or active ester method, it is not necessary to protect that group. The carboxyl group can be protected by esterification such as with a methyl, ethyl or benzyl ester. The ester group such as methyl ester can be removed with dilute sodium hydroxide solution or by conversion to the hydrazide, and the benzyl ester group can be removed with anhydrous hydrogen fluoride or by catalytic hydrogenation. The α-amino group of the peptide is protected by a conventional protective group, such as benzyloxycarbonyl, t-butoxycarbonyl or t-amyloxycarbonyl group. The benzyloxycarbonyl group is removed by catalytic hydrogenation and the t-butoxycarbonyl and t-amyloxycarbonyl groups are removed with trifluoroacetic acid. The preferred protective groups are: for the hydroxyl group of serine and of threonine, a benzyl group; for the hydroxyl group of tyrosine, a 2,6-dichlorobenzyl group; for the ξ-amino group of lysine, an o-chlorobenzyloxycarbonyl group; for the amino group in the guadinino group of arginine, a tosyl group; and for the mercapto group of cysteine, a p-methoxybenzyl group. These protective groups can be removed with anhydrous hydrogen fluoride. The acetamide methyl group can be used as a protective group for the mercapto group of cysteine. Since this group is stable in the presence of anhydrous hydrogen fluoride, it can be removed with mercuric acetate at pH 4 at the time of removal of the other groups.

Thus the protected p-PTH [53-84], protected h-PTH [51-84], protected h-PTH [46-84], protected [$Tyr^{52}$] h-PTH [52-84], protected [$Tyr^{50}$] h-PTH [50-84], protected [$Tyr^{45}$] h-PTH [45-84] and protected [$Cys^{45}$] h-PTH [45-84] are obtained. These protective groups are preferably split by acid decomposition such as one-step removal with anhydrous hydrogen fluoride to obtain the corresponding compound of formula [I].

When mercapto group of the 45th cysteine is protected with an acetamide methyl group, it can be removed with mercuric acetate at pH 4 after removal of the other protective groups with anhydrous hydrogen fluoride.

The above compound [I] can be purified by known purification methods for peptides. For example, it can be purified by column chromatography using Sephadex LH-20 (trade name), Sephadex G-50 (trade name), Dowex 1 (trade name) and carboxy methyl cellulose.

The peptide [I] can be obtained in the form of the free base or its salt, e.g. its salt with an organic acid such as acetic acid.

The peptides [I] of the present invention, i.e. h-PTH [53-84], h-PTH [51-84], h-PTH [46-84] and [Cys[45]] h-PTH [45-84] are useful for antibody production and enzyme-labelled peptides. The p-PTH [46-84] and [Cys[45]] h-PTH [45-84] are advantageous for the preparation of antibodies. Especially h-PTH [53-84] and h-PTH [51-84] are advantageously useful as controls for antibody preparation. Peptides having N-terminal tyrosine, i.e. [Tyr[52]] h-PTH [52-84], [Tyr[50]] h-PTH [50-84] and [Tyr[45]] h-PTH [45-84] are particularly useful as labelling agents on RIA. For example, [Tyr[52]] h-PTH [52-84] or [Tyr[50]] h-PTH [50-84] and chloramine T were added to aliquot radioactive iodine 125 in a phosphate buffer (pH 7.4), the mixture was stirred, sodium bisulfide was added, and a small amount of potassium iodide and serum albumin were also added. Iodine 125-labelled fractions were collected by chromatography to obtain iodine 125-conjugated compounds of tyrosine residue, i.e. the labelled compound iodine 125-[Tyr[52]] h-PTH [52-84] and the labelled compound iodine 125-[Tyr[50]] h-PTH [50-84], which are useful as RIA reagents.

The labelling with iodine 125 and its absorption on the materials of an immune reaction tube using [Tyr[52]] h-PTH [52-84] and [Tyr[50]] h-PTH [50-84] obtained in the examples hereinafter explained will be illustrated hereinbelow.

(1) Labelling with iodine 125

A solution (10 μl) of [Tyr[52]] h-PTH [52-84] (2 μg) or [Tyr[50]] h-PTH [50-84] (2 μg) and a solution (20 μg) of chloramine T (3.5 mg/ml) were added to 0.5 M phosphate buffer (pH 7.5, 50 μl) containing iodine 125-NaI (radioactivity 2 mCi), the mixture was stirred for 30 seconds and sodium bisulfide (4.5 mg/ml) solution (50 μl was added to stop the reaction. A 0.1 N acetic acid solution (0.5 ml) containing 5% human serum albumin was added thereto and the mixture was passed through a column (1×50 cm) of Sephadex G-25 for gel-filtration to remove unreacted iodine 125-NaI. There was thus obtained a labelled compound iodine 125-[Tyr[52]] h-PTH [52-84] and a labelled compound iodine 125-[Tyr[50]] h-PTH [50-84] developer: 0.1 N acetic acid solution containing 0.5% human serum albumin).

The specific activity of the thus-obtained iodine 125-[Tyr[52]] h-PTH [52-84] and iodine 125-[Tyr[50]] h-PTH [50-84] were 523 μCi/μg and 545 μCi/μg, respectively, and the yields were 75.5% and 76.7%, respectively. Two-fold superior specific activity and three- to four-fold yield were obtained as compared with labelling with h-PTH [1-34] or bovine PTH [1-84] (extracted product).

(2) Adsorption of iodine 125-labelled compound on an immune reaction tube

Aliquot portions (10.5 ml) of 0.01 M ammonium acetate solution (300,000 cpm) containing iodine 125-[Tyr[52]] h-PTH [52-84], and iodine 125-[Tyr[50]] h-PTH [50-84], respectively, were added to an immune reaction tube, which was allowed to stand, and then the contents were removed and washed with an excess of distilled water, and the residual radioactivity in the tube was measured to measure the adsorbency of the reaction tube.

The adsorption ratios of iodine 125-[Tyr[52]] h-PTH [52-84] were 33.1% for a Pyrex glass tube, 7.7% for an Eiken No. 1 tube, 5.0% for a Maruemu tube and 0.5% for a Technicon tube. The adsorption ratios of iodine 125 [Tyr[50]] h-PTH [50-84] were 30.8% for the Pyrex tube, 8.1% for the Eiken No. 1 tube, 5.5% for the Maruemu tube and 0.4% for the Technicon tube.

The absorption ratio of a control iodine 125-bovine-PTH [1-84] were 58.4% for the Pyrex tube, 15.7% for the Eiken No. 1 tube, 12.2% for the Maruemu tube and 4.5% for the Technicon tube.

The absorption ratio is calculated by the following equation:

$$\text{Adsorption ratio (\%)} = \frac{\text{residual radioactivity (cpm)}}{\text{added radioactivity (cpm)}} \times 100$$

(3) Stability (a) Iodine 125-[Tyr[52]] h-PTH [52-84] and iodine 125-[Tyr[50]] h-PTH [50-84] were stored at −20° C. for two days, 18 days, 31 days and 60 days, respectively, and subjected to gel filtration with Sephadex G-50 (column: 1×30 cm, developer: 0.1 M ammonium acetate buffer). The radioactivities thereof were observed at positions corresponding to [Tyr[52]] h-PTH [52-84] and [Tyr[50]] h-PTH, and were found to be quite stable.

(b) The adsorption activities of iodine 125-[Tyr[52]] h-PTH [52-84] and iodine 125-[Tyr[50]] h-TPH [50-84] to talc powder were 92–98% immediately after adsorption, at −20° C. for 2 days, 18 days, 31 days and 61 days. No decrease of adsorption activity was observed.

Human PTH or its C-terminal fragment can be assayed with EIA using a peptide of the formula [Ia] or a peptide with EIA using a peptide of the formula [Ia] or a peptide of the formula [Ib] (hereinafter designated as peptide [Ia] and peptide [Ib], respectively).

The reagents necessary for assaying PTH with EIA, such as antisera, antibodies or enzyme-labelled compounds are preapred as follows:

For obtaining specific antibodies using a peptide [Ia], a peptide [Ia] per se or a peptide [Ia] conjugated with a protein, such as BSA or BSA treated with alkali or sodium lauryl sulfate and mercaptoethanol for splitting the inner molecular disulfide group, is administered to mammals such as rabbits, rats, guinea pigs or mice for sensitization. For example, the above peptide [Ia] or its protein-conjugated compound is mixed with Freund's complete adjuvant and administered subcutaneously 4–7 times by injection at two-week intervals to sensitize the mammals. Serum is collected from the sensitized animals and conventionally treated by, for example, centrifugation to obtain an antiserum. The antiserum containing a high concentration of specific antibodies can be stored as is, and can be used with aliquot dilution. Specific antibodies can also be purified by conventional methods such as salting out, isoelectric precipitation, dialysis, chromatography or gel filtration.

A protein-conjugated peptide [Ia] can be obtained by using a polyfunctional reagent, for example, an aldehyde compound such as succinaldehyde, glutaraldehyde or adipoaldehyde, a diisocyanate such as hexamethylene diisocyanate or 2,4-toluenediisocyanate, 3-(2'-benzothiazolyl-dithio)propionate succinimide ester (Japanese Patent Unexamined Publ. No. 55-17302), 6-N[3-(2'-benzothiazolyl-dithio)propionyl]caproic acid succinimide ester or N-[2-(2'-pyridyl-dithio)ethyl]-3-(2'-benzothiazolyl-dithio)propionamide (Japanese Patent Unexamined Publ. No. 55-94367, No. 55-133382 or No. 55-136261), maleimide benzoate succinimide ester, N,N'-ethylene bis-maleimide, bisdiazobenzidine or diethylmalonimidate. These polyfunctional reagents can be selected with regard to the functional groups in the peptide [Ia] or protein, such as amino, carboxyl or thiol groups. A preferred example of peptide [Ia]-protein-conjugated compound is prepared from [$Cys^{45}$] h-PTH ]45-84] of peptide [Ia] and a polyfunctional reagent of 3-(2'-benzothiazolyl-dithio)propionate succinimide ester to bind the thiol group of $Cys^{45}$.

The preferred ratio for conjugation is one mole of protein such as BSA to 1–20 moles of peptide [Ia]. In the reaction, the peptide [Ia] is added to an aqueous medium of pH 7–8, and the polyfunctional reagent is added. The reaction is allowed to proceed at room temperature for 1–5 hours, and the product is purified by gel filtration. BSA is added thereto, reacted at room temperature for 1–5 hours and purified by conventional gel filtration and dialysis to prepare a peptide [Ia] conjugated with BSA.

The above specific antibody is proportionally bound with an immobilized carrier, for example, an immobilized protein carrier such as albumin or gelatin, an immobilized semi-synthetic polymer such as agarose, cellulose or dextrin treated with epichlorophydrin or bromocyanate, or a polymer or copolymer of acrylonitrile, acrylic acid, acrylic acid ester, methacrylate, methacrylate ester, vinyl alcohol, vinyl acetate, aminostyrene, acrylamide or ethylene, using the above polyfunctional reagent.

Examples of enzymes for the preparation of an enzyme-labelled peptide [Ib] in EIA are oxido-reductase, hydrolase, transferase, lyase, isomerase or ligase, for example lactate dehydrogenase, malate dehydrogenase, malic dehydrogenase, maltose dehydrogenase, lactate oxidase, malate oxidase, glucose oxidase, choline oxidase, xanthine oxidase, amino acid oxidase, sarcosine oxidase, catalase, α-amilase, β-galactosidase, lysozyme, lipase, alkaline phosphatase, amino peptidase, trypsin, papaine, α-chymotrypsin, amidase, hexokinase and glycerokinase. Appropriate spacers can previously be introduced in these enzymes. Examples of these are dialdehydes such as glutaraldehyde, reactive derivatives such as ω-amino acetic acid chloride, diamines such as bondings of dialdehyde or dicarboxylic acid with hexamethylenediamine or decamethyleneamine, S-acetylmercapto succinic anhydride and bondings of dialdehydes and 2-aminoethane thiol. Aldehydes, or amino or thiol groups can be introduced by using the above spacer-introducing reagents.

Peptide [Ib]-enzyme conjugates can be obtained by conjugating a peptide [Ib] and amino, hydroxy, carboxyl or thiol groups in the enzyme, or introduced aldehyde, amino, thiol groups in the enzyme, or by introducing aldehyde, amino, thiol or carboxyl groups therein, by using a polyfunctional reagent.

An example of preparation of the enzyme-labelled compounds of peptide [Ib]-enzyme conjugates is as follows:

A peptide [Ib] is reacted with a polyfunctional reagent at 0°–40° C. in the presence of an organic solvent such as methanol, ethanol, acetone, dioxane, dimethylsulfoxide, dimethylacetamide or tetrahydrofuran in a buffer (pH 6–8) or directly in one of these organic solvents. The ratio of the peptide [Ib] and the polyfunctional reagent is preferably equimolar. After the reaction, the reaction product is purified, if required, and the enzyme is reacted therewith, preferably in a buffer of stable pH for the enzyme. The amount of enzyme is preferably equimolar or in slight molar excess. The thus-prepared peptide [Ib]-enzyme conjugate can be purified by adsorption chromatography or gel filtration.

Various conventional EIA techniques can be used in the present invention for assaying h-PTH. Examples of these are the competition method or the sandwich method.

The details of the competition method are as follows:

A sample containing h-PTH to be assayed, an enzyme-labelled peptide [Ib] and an antiserum or antibodies of peptide [Ia] are incubated in an immunoreaction medium such as a phosphate buffer or veronal buffer at 4°–5° C. for 1–3 days. Then the immunologically-bound part (bound:B) and the non-bound free part (free:F) are separated (B-F separation). B-F separation is preferably carried out by adding normal serum of the same mammal as is used for the antiserum preparation and the antiserum thereof, incubating the mixture overnight, then centrifuging it at 3000 r.p.m. for 20–30 minutes for B-F separation. Thereafter, enzymatic activity of the precipitated enzyme-labelled compound (B) or that of the supernatant (F) is assayed. In a solid phase method, immobilized antibodies are used, for the competitive reaction, in place of the antiserum or antibodies of peptide [Ia] in the above competition method; then, after reaction, B-F separation is carried out and enzyme activity is assayed as above.

Other conventional sandwich methods can be used with the desired reagents.

The h-PTH or its C-terminal fragment can be assayed by using antibodies of peptide [Ia] and enzyme-labelled peptide [Ib] with good accuracy and simplicity. Preferably, β-galactosidaselabelled [$Cys^{45}$] h-PTH [45-84] is used for the assay.

The abbreviations used herein have the following meanings:

| | | | |
|---|---|---|---|
| BOC: | t-butoxycarbonyl | AOC: | t-amyloxycarbonyl |
| PAC: | phenacyl ester | Z—Cl: | o-chlorobenzyloxy-carbonyl |
| Bel | benzyl | Tos: | tosyl |
| Val: | L-valine | OMe: | methyl ester |
| OEt: | ethyl ester | ONP: | p-nitrophenyl ester |
| OBzl: | benzyl ester | Cys: | L-cysteine |
| OSU: | N-hydroxysuccinimide ester | Thr: | L-threonine |
| Ser: | L-serine | Glu: | L-glutamic acid |
| Asn: | L-aspartic acid | Pro: | L-proline |
| Leu: | L-leucine | Asp: | L-aspartic acid |
| MeOH: | methanol | Gly: | glycine |
| Arg: | L-arginine | Gln: | L-glutamine |
| Ala: | L-alanine | His: | L-histidine |
| Lys: | L-lysine | EtOH: | ethanol |
| BuOH: | butanol | NMP: | N-methyl-2-pyrrolidone |
| Tyr: | L-tyrosine | $Et_3N$: | triethylamine |
| TosoH: | p-toluenesulfonic acid | ether: | diethyl ether |
| TFA: | influoroacetic acid | DMF: | dimethylformamide |
| THF: | tetrahydrofuran | TBA: | tribenzylamine |
| NMM: | N'-methylmorpholine | HOBT: | 1-hydroxybenzotriazole |
| WSCI: | N-ethyl-N'-dimethylaminopropyl-carbodimide | | |

The following examples illustrate the present invention. In the example, the following carriers and developing solvents for thin layer chromatography (TLC) are used:

Carrier: Silica-gel G.

Developer:

1. Chloroform-methanol-acetic acid (95:5:3)
2. Chloroform-methanol-acetic acid (85:15:5)
3. Chloroform-methanol-acetic acid (85:10:5)
4. Chloroform-methanol-acetic acid (80:25:2)
5. Benzene-ethyl acetate (1:1)
6. Benzene-ethyl acetate (2:1)
7. Chloroform-ethanol-ethyl acetate (5:2:5)
8. Chloroform-ethanol-ethyl acetate (10:1:5)

Carrier: Merck cellulose.

Developer:

9. Butanol-pyridine-acetic acid-water (2:2:2:3)
10. Butanol-pyridine-acetic acid-water (1:1:1:2)

Amino acid analysis is carried out as follows:

The sample is hydrolyzed in 6 N HCl (anisole is added for a protected peptide, if necessary) at 110° C. for 24–45 hours in a sealed tube and the hydrolyzate is dried in vacuo.

EXAMPLE 1

H—Pth (53-84);
H—Lys—Lys—Lys—Glu—Asp—Asn—Val—Leu—Val—Glu—Ser—His—Glu—Lys—Ser—Leu—Gly—Glu—Ala—Asp—Lys—Ala—Asp—Val—Asp—Val—Leu—Thr—Lys—Ala—Lys—Ser—Gln'Oh

(1) P(83-84): BOC—Ser(Bzl)—Gln—OBzl [1]

BOC—Gln—OBzl (181.4 g, 0.242 M) was dissolved in TFA (270 ml) and the mixture was stirred at room temperature for 45 minutes. After TFA was distilled off in vacuo, ether was added to the residue and the precipitate was collected. The precipitate was dissolved in DMF (270 ml), and HOBT (32.67 g, 0.242 M), BOC—Ser(Bzl)—OH (67.35 g, 0.242 M) and WSCI (44.29 ml, 0.242 M) were added thereto and the mixture was stirred overnight. The DMF was distilled off, and the residue was dissolved in ethyl acetate (440 ml), then washed with 1 N HCl, 5% sodium bicarbonate and water. The solution was dried by adding anhydrous sodium sulfate and filtered, then dried in vacuo. Recrystalization was effected from ethyl acetate-hexane to obtain substance [1] (101.43 g, yield: 81.6%).

m.p.: 121°–123° C.

TLC: $Rf_7=0.73$ $[\alpha]_D^{27}=-14.12$ (c=1.0, DMF)

| Elementary analysis [$C_{27}H_{35}O_7N_9$]: | C % | H % | N% |
|---|---|---|---|
| Found | 62.98 | 7.03 | 8.01 |
| Calculated | 63.14 | 6.87 | 8.18 |

(2) P(82-84): BOC—Lys(Z—Cl)—Ser(Bzl)—Gln—OBzl [2]

TFA (440 ml) was added to substance [1] (98.87 g, 192.5 mM), and the mixture was stirred at room temperature for 30 minutes. The TFA was distilled off in vacuo. The residue was dissolved in DMF (330 ml). HOBT (28.6 g), and a DMF solution of BOC—Lys(Z—Cl)—OH [BOC—Lys(Z—Cl)—OH.TBA (103.33 g, 1.1 molar excess)] were treated with ethyl acetate-1 N HCl. The ethyl acetate layer was dried with anhydrous sodium sulfate and dried in vacuo, and WSCI [38.72 ml (1.1 molar excess)] was added thereto. The mixture was stirred at room temperature for two days. The DMF was distilled off in vacuo and ice water was added to the residue, then the thus-formed precipitate was collected. Recrystallization was effected three times from ethanol-hexane to obtain substance [2] (111.06 g, yield: 71.2%).

m.p.: 145°–147° C.

TLC: $Rf_1=0.32$, $Rf_7=0.76$ $[\alpha]_D^{27}=-13.1°$ (c=1.0, DMF)

| Elementary analysis [$C_{41}H_{52}O_{10}N_5Cl$]: | C % | H % | N % |
|---|---|---|---|
| Found | 61.02 | 6.65 | 8.74 |
| Calculated | 60.77 | 6.47 | 8.65 |

(3) P(80-81): BOC—Lys(Z—Cl)—Ala—OMe [3]

BOC—Lys(Z—Cl)—OH.TBA (234.24 g) suspended in ethyl acetate was washed with 1 N HCl and water, and dried with anhydrous sodium sulfate. The suspension was dried in vacuo and dissolved in DMF (400 ml). H—Ala—OMe.HCl (67.0 g), HOBT (64.8 g) and WSCI (87.84 ml) were added thereto and the mixture was stirred at room temperature overnight. The DMF was distilled off in vacuo and the residue was dissolved in ethyl acetate (2 lit.) was washed with 5% sodium bicarbonate, 1 N HCl and water. After drying with sodium sulfate, the solution was dried in vacuo. Recrystallization was effected from ethyl acetate-hexane to obtain substance [3] (231.8 g, yield: 96.6%).

m.p.: 58°–60° C.

TLC: $Rf_1=0.77$ $[\alpha]_D^{27}=-17.16$ (c=1.0, DMF)

| Elemantary analysis [$C_{23}H_{34}O_7N_3Cl$]: | C % | H % | N % |
|---|---|---|---|
| Found | 54.96 | 6.78 | 8.56 |
| Calculated | 55.25 | 6.85 | 8.40 |

(4) P(79-81): BOC—Thr(Bzl)—Lys(Z—Cl)—Ala—OMe [3]

Substance [3] (174.99 g, 0.35 M) was added to TFA (500 ml) and the mixture was stirred at room temperature for 50 minutes. The TFA was distilled off in vacuo. The residue was dissolved in ethyl acetate and washed with 5% sodium bicarbonate and water. The solution was dried with anhydrous sodium sulfate, and dried in vacuo.

The residue was dissolved in DMF (400 ml). HOBT (49.95 g, 1.05 molar excess), BOC—Thr(Bzl)—OH (114.33 g, 1.05 molar excess) and WSCI (67.7 ml, 1.05 molar excess) were added thereto and the mixture was stirred at room temperature overnight. The DMF was removed in vacuo and ice water was added to the residue. The precipitate was collected and recrystallized from hot ethanol to obtain substance [4] (99.31 g).

The mother liquor was concentrated in vacuo. The residue was dissolved in chloroform and washed four times with 5% sodium bicarbonate, twice with 1 N HCl and twice with water. After dehydrating with anhydrous sodium sulfate, the solution was dried in vacuo. The residue was purified by silica-gel column chromatography [developer: chloroform-ethanol-acetic acid (5:1:5)] to obtain substance [4] (35.09 g). The fractions containing impurities were reserved for use in the next column chromatography purification step.

Substance [3] (22.5 g, 45 mM) was added to TFA (70 ml) and the mixture was stirred at room temperature for 45 minutes. The TFA was removed in vacuo and the residue was dissolved in DMF (50 ml), then adjusted to pH 7 by adding NMM. HOBT (6.68 g, 1.1 molar excess), BOC—Thr(Bzl)—OH(15.31 g, 1.1 molar excess) and WSCI (9.06 ml, 1.1 molar excess) were added thereto and the mixture was stirred overnight. After distilling off the DMF in vacuo, the residue was dissolved in chloroform (200 ml) and washed with 5% sodium bicarbonate, 1 N HCl and water. The solution was dried with anhydrous sodium sulfate and dried in vacuo. The residue was mixed with the reserved fractions containing impurities and purified by silica gel column chromatography. The corresponding fraction was dried in vacuo and reprecipitated twice with chloroform-hexane to obtain substance [4] (48.80 g). Total yield: 183.2 g.

m.p.: 132°-134° C.

TLC: $Rf_7=0.85$

| Elementary analysis [$C_{34}H_{47}O_9N_4Cl$]: | | | |
|---|---|---|---|
| | C % | H % | N % |
| Found | 59.06 | 7.05 | 7.41 |
| Calculated | 59.08 | 6.85 | 8.11 |

(5) P(77-78): BOC—Val—Leu—OEt [5]

BOC—Val—OH (101.99 g, 0.47 M), H—Leu—O-Et.HCl (91.98 g, 0.47 M), HOBT (63.45 g) and WSCI (86.01 ml, 0.47 M) dissolved in THF (400 ml) was stirred overnight. The THF was distilled off in vacuo, and the residue was dissolved in ethyl acetate (400 ml) and washed with 5% sodium bicarbonate, 1 N HCl and water. After drying with anhydrous sodium sulfate, the residue was dried in vacuo. Recrystallization was effected from ethyl acetate-hexane to obtain substance [5] (153.7 g, yield: 91.2%).

m.p.: 108°-110° C.

TLC: $Rf_1=0.63$ $[\alpha]_D^{27}=-25.78$ (c=1.0, DMF)

| Elementary analysis [$C_{18}H_{34}O_5N_2$]: | | | |
|---|---|---|---|
| | C % | H % | N % |
| Found | 60.35 | 9.42 | 8.39 |
| Calculated | 60.31 | 9.56 | 7.82 |

(6) P(77-78): BOC—Val—Leu—OH [6]

To substance [5] (134.43 g, 0.375 M) dissolved in ethanol (400 ml) was added 1 N NaOH (412.5 ml, 1.1 molar excess) with ice cooling and the mixture was stirred for 1.5 hours. 1 N NaOH (37.5 g, 0.1 molar excess) was added and the mixture was further stirred for one hour. 1 N HCl (75 ml) was added thereto to adjust to pH 5. The solution was washed with ether. 1 N HCl (400 ml) was added to the aqueous layer and the mixture was extracted with ethyl acetate. After drying the ethyl acetate layer, it was dried in vacuo and recrystallized from ethyl acetate-hexane to obtain substance [6] (119.66 g, yield: 96.6%).

TLC: $Rf_1=0.35$, $Rf_7=0.58$

| Elementary analysis [$C_{16}H_{30}O_5N_2$]: | | | |
|---|---|---|---|
| | C % | H % | N % |
| Found | 57.83 | 9.40 | 8.78 |
| Calculated | 58.16 | 9.15 | 8.48 |

(7) P(77-81): BOC—Val—Leu—Thr(Bzl)—Lys(Z—Cl-)—Ala—OMe [7]

Substance [4] (182 g, 0.263 M) was added to TFA (500 ml) and the mixture was stirred at room temperature for 50 minutes. The TFA was distilled off and hexane was added to the residue. A precipitated oily substance was separated by decantation and dissolved in DMF (350 ml), which was adjusted to pH 6.5 by adding NMM. HOBT (42.61 g, 1.2 molar excess), substance [6] (104.28 g, 1.2 molar excess) and WSCI (57.8 g, 1.2 molar excess) were added thereto and the mixture was stirred at room temperature for 1.5 hours. When the reaction mixture became solid and impossible to stir, further DMF (200 ml) was added; then the mixture was allowed to stand overnight at room temperature and at 30° C. for 4 hours. Ice water was added to the reaction mixture and the precipitate collected, which was dissolved in chloroform (2.5 lit.) and washed with 5% sodium bicarbonate, 1 N HCl and water. Chloroform was distilled off in vacuo and the residue was recrystallized from chloroform-ether-hexane to obtain substance [7] (224.68 g, yield: 94.9%).

m.p.: 219°-221° C.

TLC: $Rf_1=0.15$, $Rf_8=0.68$ $[\alpha]_D^{27}=-11.72$ (c=1.0, DMF)

| Elementary analysis [$C_{45}H_{67}O_{11}N_6Cl$]: | | | |
|---|---|---|---|
| | C % | H % | N % |
| Found | 59.80 | 7.56 | 9.83 |
| Calculated | 59.82 | 7.48 | 9.30 |

(8) P(77-81): BOC—Val—Leu—Thr(Bzl)—Lys(Z—Cl)—Ala—OH [8]

A 90% ethanol solution (800 ml) of 1 N KOH was added with ice cooling to substance [7] (72.3 g, 80 mM) dissolved in chloroform (720 ml) and the mixture was stirred at 0°-5° C. for 40 minutes. 1 N HCl (800 ml) was added thereto with ice cooling and the mixture was extracted with chloroform (500 ml) twice. The chloroform layer was washed with water, dried by adding anhydrous sodium sulfate, and then dried in vacuo. The residue was purified by silica gel column chromatography [developer: chloroform-ethanol-ethyl acetate (5:1:5)]. The corresponding fraction was dried in vacuo and recrystallized three times from chloroform-methanol-ether-hexane to obtain substance [8].

The above operations were repeated three times to hydrolyze substance [7] (216.9 g) to obtain substance [9] (156.07 g, yield: 73.1%).

m.p.: 180°-183° C.

TLC: $Rf_3=0.69$ $[\alpha]_D^{27}=-7.54$ (c=1.0, DMF)

| Elementary analysis [$C_{44}H_{65}O_{11}N_6Cl.\frac{1}{2}H_2O$]: | C % | H % | N % |
|---|---|---|---|
| Found | 58.94 | 7.67 | 9.64 |
| Calculated | 58.82 | 7.40 | 9.35 |

Amino acid analysis [sample 3.1 mg/1 ml 6 N HCl+0.1 ml anisole, hydrolyzed at 110° C. for 45 hours]: Thr 0.96 (1), Ala 1, Val. 0.93 (1), Leu 0.94 (1), Lys 1.01 (1).

(9) P(77-84):
BOC—Val—Leu—Thr(Bzl)—Lys(Z—Cl-)—Ala—Lys(Z—Cl)—Ser(Bzl)—Gln—OBzl [9]

Substance [2] (104.5 g, 129 mM) added to TFA (400 ml) was stirred at room temperature for 40 minutes. The TFA was distilled off in vacuo and ether was added to the residue. The precipitate was collected and dissolved in DMF (500 ml). HOBT (20.9 g, 1.2 molar excess), substance [8] (137.7 g, 1.2 molar excess) and WSCI (28.3 ml, 1.2 molar excess) were added thereto, and the mixture was adjusted to pH 7 by adding NMM and stirred overnight. The reaction mixture became a gel, and then further DMF (150 ml) and WSCI (12.8 ml) were added and the mixture was stirred overnight. Ice water was added to the reaction mixture, and the precipitate was collected and washed five times with hot methanol to obtain substance [9] (185.36 g, yield: 90.68%).

TLC: $Rf_2=0.85$ $[\alpha]_D^{27}=-12.84$ (c=1.0, DMF)

| Elementary analysis [$C_{10}H_{107}O_{18}N_{11}Cl_2$]: | C % | H % | N % |
|---|---|---|---|
| Found | 60.61 | 7.04 | 10.38 |
| Calculated | 60.75 | 6.82 | 9.74 |

Amino acid analysis [sample 3.1 mg/1 ml 6 N HCl+0.1 ml anisole, hydrolyzed at 110° C. for 45 hours]: Thr 0.93 (1), Ser 0.91 (1), Glu 1.01 (1), Ala 1, Val 0.74 (1), Leu 0.75 (1), Lys 2.01 (2).

(10) P(76-84):
BOC—Asp(OBzl)—Val—Leu—Thr(Bzl)—Lys(-Z—Cl)—Ala—Lys(Z—Cl)—Ser(Bzl)—Gln—OBzl [10]

Substance [9] (183.5 g, 116 mM) added to TFA (500 ml) was stirred at room temperature for 65 minutes and then the TFA was distilled off. Ether was added to the residue, and the precipitate was collected which was dissolved in DMF (900 ml). HOBT (18.8 g, 1.2 molar excess), BOC—Asp(OBzl)—OH (45.0 g, 1.2 molar excess) and WSCI (25.5 ml, 1.2 molar excess) were added thereto, and the pH was adjusted to 7 by adding NMM, then the mixture was stirred at room temperature overnight. The DMF was distilled off in vacuo and ice water was added to the residue. The precipitate was collected and washed twice with hot methanol. The insolubles were dissolved in hot DMF and ethanol was added thereto. The precipitate was collected, suspended and filtered to obtain substance [10] (205.5 g, yield: 99.14%).

m.p.: 259°-262° C.

TLC: $Rf_2=0.81$ $[\alpha]_D^{27}=-13.7$ (c=1.0, DMF)

| Elementary analysis [$C_{51}H_{118}O_{21}N_{12}Cl_2$]: | C % | H % | N % |
|---|---|---|---|
| Found | 61.01 | 6.84 | 9.54 |
| Calculated | 61.16 | 6.66 | 9.41 |

(11) P(75-84):
BOC—Val—Asp(OBzl)—Val—Leu—Thr(Bzl)—Lys(-Z—Cl)—Ala—Lys(Z—Cl)—Ser(Bzl)—Gln—OBzl [11]

Substance [10] (196.55 g, 0.11 M) was added to TFA (500 ml), the mixture was stirred at room temperature for 60 minutes, and the TFA was removed in vacuo. Ether was added to the residue, and the precipitate was collected and then dissolved in DMF (1.3 lit.) HOBT (19.3 g, 1.3 molar excess), BOC—Val—OH (31.1 g, 1.3 molar excess) and WSCI (26.2 ml, 1.3 molar excess) were added thereto with stirring, the pH was adjusted to 7 by adding NMM and the mixture was stirred at room temperature. After one hour the reaction mixture gelled and was allowed to stand overnight. NMP (400 ml), 2,4-dinitrophenol (20.2 g) and WSCI (26.2 ml, 1.3 molar excess) were added thereto. Gelling occurred after about 10 minutes, and the material was allowed to stand overnight. Ice and 5% sodium bicarbonate solution was added. The precipitate was collected, and was washed three times with water and four times with hot methanol to obtain substance [11] (203.74 g, yield: 98.2%).

m.p.:267°-270° C.

TLC: $Rf_3=0.56$

| Elementary analysis [$C_{96}H_{127}O_{22}N_{13}Cl_2.H_2O$]: | C % | H % | N % |
|---|---|---|---|
| Found | 60.25 | 6.78 | 9.82 |
| Calculated | 60.55 | 6.83 | 9.56 |

Amino acid analysis: [sample 3.1 mg/1 ml 6 N HCl+0.1 ml anisole, hydrolysis for 48 hours at 110° C.]: Asp 1.04 (1), Thr 0.83 (1), Ser 0.78 (1), Glu 1.03 (1), Ala 1.08 (1), Leu 1, Val 1.87 (2), Lys 2.19 (2).

(12) P(74-84):
BOC—Asp(OBzl)—Val—ASp(OBzl)—Val—Leu—Thr(Bzl)—Lys(Z—Cl)—Ala—Lys(-Z—Cl)—Ser(Bzl)—Gln—OBzl [12]

Substance [11] (151.2 g, 0.08 M) dissolved in methylene chloride (100 ml) and TFA (450 ml) was stirred at room temperature for 40 minutes, then the TFA was removed in vacuo. Ether was added to the residue. DMF (500 ml) and NMP (1 lit.) were added to the precipitate to dissolve it. Ice and 5% sodium bicarbonate was added thereto. The thus-formed precipitate was collected, washed with water and dried. A mixture of DMF (500 ml) and NMP (1 lit.) was added to dissolve the material and BOC-Asp(OBzl)-OSU (44.0 g, 1.3 molar excess), HOBT (1.4 g, 0.13 molar excess) and NMM (11.4 ml, 1.3 molar excess) were added thereto, then the mixture was stirred at room temperature overnight. The reaction mixture was poured into ice water, and the thus-formed precipitate was collected and was suspended in hot methanol. After cooling, the precipitate was filtered. This operation was repeated twice to obtain substance [12] (157.6 g, Yield: 94.2%).

TLC: $Rf_3=0.56$

| Elementary analysis [$C_{107}H_{135}O_{25}N_{14}Cl_2$]: | C % | H % | N % |
|---|---|---|---|
| Found | 61.35 | 6.66 | 9.90 |
| Calculated | 61.45 | 6.65 | 9.38 |

Amino acid analysis [6 N HCl/anisole, 110° C., 48 hours]: Asp 1.86 (2), Thr 0.87 (1), Ser 0.71 (1), Glu 1.01 (1), Ala 1.00 (1), Val 1.91 (2), Leu 1, Lys 2.01 (2).

(13) P(72-73): BOC—Lys(Z—Cl)—Ala—OH [13]

1 N NaOH (115.2 ml, 1.2 molar excess) was added at 0° C. to substance [3] (48.0 g, 96 mM) dissolved in ethanol (100 ml), and the mixture was stirred for 50 minutes. 1 N HCl (19 ml) was added to adjust the pH to 6, and the ethanol was distilled off at 35° C. Ethyl acetate, ice water and 1 N HCl (96 ml) were added to the residue for extraction. The ethyl acetate layer was washed with water, dried by adding anhydrous sodium sulfate then dried in vacuo. The residue was recrystallized from ethyl acetatehexane to obtain substance [13] (45.90 g, yield: 98.4%).

m.p.: 116°-119° C.

TLC: $Rf_7=0.44$

| Elementary analysis [$C_{22}H_{32}O_7N_3Cl$]: | C % | H % | N % |
|---|---|---|---|
| Found | 54.57 | 6.91 | 8.95 |
| Calculated | 54.37 | 6.64 | 8.65 |

(14) P(72-84):
BOC—Lys(Z—Cl)—Ala—Asp(OBzl)—Val—Asp-(Obzl)—Val—Leu—Thr(Bzl)—Lys(ZCl)—Ala—Lys(-Z—Cl)—Ser(Bzl)—Gln—OBzl [14]

Methylene chloride (60 ml) and TFA (360 ml) were added to substance [12] (125.46 g, 60 mM), the mixture was stirred at room temperature for 55 minutes, then the TFA was distilled off. Ether was added to the residue and the precipitate was collected. DMF (600 ml) and NMP (600 ml) was added to dissolve the precipitate. Ice and 5% sodium bicarbonate were added thereto. The thus-precipitated material was collected, washed three times with water, again washed with methanol and ether and dried. NMP (1200 ml) and DMF (600 ml) were added thereto to dissolve the material. HOBT (10.56 g, 1.3 molar excess), substance [13] (37.92 g, 1.3 molar excess) and WSCI (14.28 g, 1.3 molar excess) were added thereto, and the mixture was stirred at room temperature for 3 days. The reaction mixture was poured into ice water, and the precipitate was collected, washed three times with water, then washed twice with hot methanol. The material was further washed with ether, and dried to obtain substance [14] (142.74 g, yield: 96.7%).

| Elementary analysis [$C_{124}H_{161}O_{29}N_{27}Cl_3$]: | C % | H % | N % |
|---|---|---|---|
| Found | 60.30 | 6.79 | 9.70 |
| Calculated | 60.54 | 6.60 | 9.68 |

Amino acid analysis [6 N HCl/anisole, 110° C., 48 hours]: Asp 1.86 (2), Thr 0.85 (1), Ser 0.67 (1), Glu 1.02 (1), Ala 1.90 (2), Val 1.93 (2), Leu 1, Lys 2.93 (3).

(15) P(71-84):
BOC—Asp(OBzl)—Lys(Z—Cl)Ala—Asp(OBzl)—Val—Asp(OBzl)—Val—Leu—Thr(Bzl)—Lys(-Z—Cl)—Ala—Lys(Z—Cl)—Ser(Bzl)—Gln—OBzl [15]

Substance [14] was added to TFA (420 ml), and the mixture was stirred at room temperature for 55 minutes, and the TFA was distilled off in vacuo. Ether was added to the residue, and the precipitate was collected, then NMP (720 ml) and DMF (720 ml) were added thereto to dissolve the precipitate. The mixture was poured into ice and 5% sodium bicarbonate solution; and the thusformed precipitate was collected, washed three times with water, once each with methanol and ether. NMP (840 ml) and DMF (840 ml) were added thereto to dissolve the material. HOBT (0.732 g, 0.14 molar excess), 2,4-dinitrophenol (11.93 g, 1.2 molar excess), BOC-Asp(OBzl)-OSU (3.18 g, 1.2 molar excess) and NMM (5.94 ml, 1.4 molar excess) were added and the mixture was stirred at room temperature for two days. NMP (120 ml) and DMF (60 ml) were added again to the reaction mixture to dissolve the material. BOC-Asp (OBzl)-OSU (4.56 g, 0.2 molar excess) and NMM (1.19 ml, 0.2 molar excess) were added and the mixture was further stirred at room temperature for two days. The reaction mixture was poured into ice water, and the precipitate was collected and washed with water and was suspended in hot methanol. After cooling, the precipitate was filtered. This operation was repeated for three times to obtain substance [15] (136.72 g, yield: 95.0%).

| Elementary analysis [$C_{135}H_{172}O_{32}N_{18}Cl_3$]: | C % | H % | N % |
|---|---|---|---|
| Found | 60.33 | 6.55 | 9.76 |
| Calculated | 60.83 | 6.51 | 9.46 |

Amino acid analysis [6 N HCl/anisole, 110° C., 48 hours]: Asp 2.60 (3), Thr 0.83 (1), Ser 0.65 (1), Glu 1.00 (1), Ala 1.81 (2), Val 1.92 (2), Leu 1, Lys 2.85 (3).

(16) P(70-84):
BOC—Ala—Asp(OBzl)—Lys(Z—Cl)—Ala—Asp-(OBzl)—Val—Asp(OBzl)—Val—Leu—Thr(Bzl)—Lys(Z—Cl)—Ala—Lys(Z—Cl)—Ser(Bzl)—Gln—OBzl [16]

Substance [15] was added to TFA (325 ml), and the mixture was stirred at room temperature for 70 minutes and the TFA was distilled off in vacuo. Ether was added to the residue. The precipitate was collected and NMP (600 ml) and DMF (600 ml) were added thereto to dissolve the material, then 5% sodium bicarbonate was added. The precipitate was collected and washed three times with water and once with methanol. The precipitate was dissolved in NMP (720 ml) and DMF (720 ml), 2,4-dinitrophenol (9.0 g), HOBT (0.55 g, 0.1 molar excess), BOC—Ala—OSU (17.52 g, 1.5 molar excess) and NMM (6.72 ml, 1.5 molar excess) were added and the mixture was stirred at room temperature overnight. Further BOC—Ala—OSU (2.34 g) and NMM (0.9 ml) were added thereto and the mixture was stirred at room temperature for 5 days. The reaction mixture was poured into ice water, the precipitate collected, and washed three times with water and twice with methanol to obtain the substance [16] (109.78 g, yield: 98.3%).

m.p.: over 280° C. (decomp.)

Amino acid analysis [6 N HCl/anisole, 110° C., 48 hours]: Asp 2.57 (3), Thr 0.84 (1), Ser 0.67 (1), Glu 1.00 (1), Ala 2.53 (3), Val 1.98 (2), Leu 1 , Lys 2.79 (3).

(17) P(69-84):

BOC—Glu(OBzl)—Ala—Asp(OBzl)—Lys(Z—Cl)—Ala—Asp(OBzl)—Val—Asp(Obzl)—Val—Leu—Thr(Bzl)—Lys(Z—Cl)—Ala—Lys(Z—Cl)—Ser(Bzl)—Gln—OBzl [17]

Substance [16] (85.38 g, 31.2 mM) was added to TFA (280 ml), the mixture was stirred at room temperature for 60 minutes and the TFA was distilled off. Ether was added to the residue, the precipitate was collected, dissolved by adding DMF (540 ml) and NMP (540 ml) and the solution was added to a mixture of 5% sodium bicarbonate and ice. The precipitate was washed three times with water and once with methanol. This was dissolved in DMF (600 ml) and NMP (780 ml). 2,4-dinitrophenol (6.89 g, 1.2 molar excess), HOBT (0.59 g, 0.14 molar excess), BOC—Glu(OBzl)—OSU (18.97 g, 1.4 molar excess) and NMM (4.8 ml, 1.4 molar excess) were added thereto and the mixture was stirred at room temperature for three days. BOC—Glu(OBzl)—OSU (2.71 g, 0.2 molar excess) dissolved in DMF (60 ml) and NMP (50 ml) and NMM (0.64 ml, 1.4 molar excess) were added thereto and the mixture was stirred further at room temperature for three days. Additionally, the same amount of BOC—Glu(OBzl)—OSU and NMM as above was added and stirred at room temperature overnight. The reaction mixture was poured into ice water, and the thus-formed precipitate was collected and washed three times with water. The precipitate was suspended in hot methanol, cooled and filtered. This operation was repeated three times to obtain substance [17] (88.97 g, yield: 96.5%).

Amino acid analysis [6 N HCl/anisole, 110° C., 24 hours]: Asp 2.66 (3), Thr 0.91 (1), Ser 0.78 (1), Glu 1.76 (2), Ala 2.65 (3), Val 1.97 (2), Leu 1, Lys 2.88 (3).

(18) P(66-68): BOC—Ser(Bzl)—Leu—Gly—OBzl [18]

WSCI (33.69 ml) was added dropwise to BOC—Leu—OH.$H_2O$ (45.64 g), H—Gly—OBzl.TosOH (61.87 g) and HOBT (24.87 g) dissolved in THF (200 ml) with cooling and the mixture was stirred at room temperature overnight. The reaction mixture was concentrated in vacuo to obtain an oily material which was dissolved in ethyl acetate (600 ml), and washed each of three times with 5% sodium bicarbonate, 1 N HCl and water. The organic layer was dried by adding anhydrous sodium sulfate and dried in vacuo to obtain an oily substance (69.0 g, yield: 99%). This was dissolved in methylene chloride (10 ml), TFA (250 ml) was added at 5° C. and the mixture was stirred at room temperature for 20 minutes. The TFA was distilled off in vacuo, DMF (200 ml) was added to the residue and the mixture was neutralized by adding NMM at 0° C. HOBT (20.7 g, 0.19 M), BOC—Ser(Bzl)—OH (56 g, 0.19 M) and WSCI (34.8 ml, 0.19 M) were added thereto and the mixture was stirred at room temperature overnight. The DMF was removed in vacuo, and ethyl acetate was added to the residue, which was then washed with 5% sodium bicarbonate, 1 N HCl and water. After drying with anhydrous sodium sulfate, the mixture was concentrated in vacuo. Hexane was added to the residue and the precipitate was collected by filtration. Recrystallization was effected from ethyl acetate-hexane and ethyl acetate-ether-hexane to obtain substance [18] (72.47 g, yield: 72.0%)

m.p.: 112°-113° C.

TLC: $Rf_5=0.55$

| Elementary analysis [$C_{30}H_{41}O_7N_3$]: | C % | H % | N % |
|---|---|---|---|
| Found | 65.06 | 7.75 | 7.56 |
| Calculated | 64.84 | 7.44 | 7.56 |

(19) P(65-68):

BOC—Lys(Z—Cl)—Ser(Bzl)—Leu—Gly—OBzl [19]

TFA (250 ml) was added at 5° C. to substance [18] (72.47 g, 0.13 M) dissolved in methylene chloride (20 ml), and the mixture was stirred at room temperature for 20 minutes. The TFA was removed in vacuo and ether was added to the residue. The precipitate was collected and DMF was added thereto. NMM was added at 5° C. to neutralize the solution.

Ethyl acetate (200 ml) was added to BOC—Lys(Z—Cl)—OH.TBA (70 g, 0.143 M) and the mixture was washed twice with 1 N HCl and water. The ethyl acetate layer was dried with anhydrous magnesium sulfate and concentrated in vacuo. DMF (100 ml) was added to the obtained oily material to prepare a DMF solution of BOC—Lys(Z—Cl)—OH.

To the above neutralized DMF solution were added HOBT (19.3 g), a DMF solution of BOC—Lys(Z—Cl)—OH and WSCI (26.2 ml, 0.143 M) and the mixture was stirred at room temperature overnight. The DMF was distilled off in vacuo, ethyl acetate (400 ml) was added to the residue and the mixture was washed three times with 5% sodium bicarbonate, twice with 1 N HCl and twice with water. The organic layer was dried with anhydrous magnesium sulfate and concentrated in vacuo. Ether and hexane were added to the residue, and the thus-precipitated material was collected and recrystallized from ethyl acetate-methanol-hexane to obtai substance [19] (104 g, yield: 94.6%).

m.p.: 128°-130° C.

TLC: $Rf_1=0.51$, $Rf_2=0.88$

| Elementary analysis [$C_{44}H_{58}O_{10}N_5Cl$]: | C % | H % | N % |
|---|---|---|---|
| Found | 61.96 | 7.02 | 7.91 |
| Calculated | 62.00 | 6.86 | 8.22 |

Amino acid analysis [1 μM/6 N HCl 0.3 ml, 105° C., 20 hours]: Ser 0.92 (1), Gly 0.98 (1), Leu 1, Lys 0.99 (1).

(20) P(65-68):

BOC—Lys(Z—Cl)—Ser(Bzl)—Leu—Gly—OH [20]

Methanol (600 ml) was added to substance [19] (85.3 g), and 1 N NaOH (120 ml) was added thereto with stirring at 5° C.; then the mixture was stirred at room temperature for three hours. After adding 1 N HCl (20 ml) at 5° C., the methanol was distilled off in vacuo. 1 N HCl (100 ml) was added to the aqueous solution of the residue at 5° C., which was then extracted with chloroform (500 ml). The chloroform layer was washed with water, dried with anhydrous sodium sulfate and concentrated in vacuo. Hexane was added to the residue, and the precipitate was collected and rcrystallized from ethyl acetate to obtain substance [20] (66.21 g, yield: 87%).

m.p.: 156°-158° C.
TLC: $Rf_2=0.63$

| Elementary analysis [$C_{37}H_{52}O_{10}N_5Cl$]: | C % | H % | N % |
|---|---|---|---|
| Found | 58.49 | 6.95 | 9.09 |
| Calculated | 58.30 | 6.88 | 9.19 |

Amino acid analysis [1 μM/0.3 ml, 6 N HCl, 105° C., 20 hours]: Ser 0.92 (1), Gly 0.97 (1), Leu 1, Lys 0.99 (1).

(21) P(64-68):
BOC—Glu(OBzl)—Lys(Z—Cl)—Ser(Bzl)—Leu—Gly—OH)[21]

Methylene chloride (300 ml) was added to substance [20] (66.2 g, 87 mM), and TFA (250 ml) was added at 5° C. and the mixture was stirred at room temperature for 45 hours. The TFA was distilled off in vacuo and ether was added to the residue. The precipitate was collected and dissolved in DMF (100 ml), which was neutralized by adding NMM at 5° C. DMF (500 ml) was again added due to the formation of a precipitate. BOC—Glu(OBzl)—OSU (50 g, 113 mM) and HOBT (1.53 g, 11.3 mM) were added thereto, and the mixture was neutralized with NMM and stirred at room temperature overnight. DMF was removed off in vacuo and the residue was poured into water. The thus-obtained precipitate was washed with water and dried. Recrystallization was effected twice from acetone-methanol to obtain substance [21] (63.85 g, yield: 73.5%).
m.p.: 165°-167° C. (decomp.)
TLC: $Rf_4=0.72$

| Elementary analysis [$C_{49}H_{60}O_{14}N_6Cl$]: | C % | H % | N % |
|---|---|---|---|
| Found | 59.61 | 6.76 | 8.31 |
| Calculated | 59.00 | 6.57 | 8.42 |

Amino acid analysis [0.927 mg/0.3 ml 6 N HCl, 105° C., 24 hours]: Ser 0.92 (1), Glu 0.99 (1), Gly 0.97 (1), Leu 1, Lys (0.99 (1).

(22) P(62-63): BOC—Ser(Bzl)—His—$NHNH_2$ [22]

THF (150 ml), H—His—OMe.2HCl (31.5 g, 0.13 M) and HOBT (17.6 g, 0.13 M) were added to BOC—Ser(Bzl)—OH (37 g, 0.125 m). WSCI (23.8 ml, 0.13 M) was added thereto, and DMF (150 ml) was added and the mixture was stirred at room temperature overnight. HOBT (4.4 g) and WSCI (6 ml) were again added, then the mixture was stirred at room temperature overnight. The solvents were distilled off in vacuo. The residual oily material was dissolved in ethyl acetate and washed three times with 5% sodium bicarbonate and water. After drying with anhydrous magnesium sulfate, it was concentrated in vacuo. Hexane was added to the residue, the precipitate was collected and recrystallized from ethyl acetate-ether-hexane to obtain crude BOC—Ser(Bzl)—His—OMe(TLC: $Rf_3=0.56$) (46.1 g).

The above produce (44.6 g) was dissolved in DMF (300 ml). Hydrazine hydrate (100%) (100 ml) was added thereto and the mixture was stirred at room temperature overnight. The DMF was removed in vacuo. The residue was extracted eight times with ethyl acetate and the extract was washed with a small amount of water, then dried with anhydrous magnesium sulfate. The solution was concentrated in vacuo, hexane was added to the residue and the precipitate was collected, which was purified by silical-gel chromatography [developer: chloroform-methanol-ethyl acetate (5:0-1:5)]. The corresponding fractions were collected, dried in vacuo and recrystallized from benzene-hexane (small amount). After being allowed to stand in a refrigerator, the precipitated crystals were recrystallized twice from ethyl acetate-methanol-hexane to obtain substance [22].
m.p.: 125°-129° C.
TLC: $Rf_4=0.70$, $Rf_7=0.14$

| Elementary analysis [$C_{21}H_{30}O_5N_6$]: | C % | H % | N % |
|---|---|---|---|
| Found | 56.30 | 6.98 | 18.54 |
| Calculated | 56.49 | 6.77 | 18.82 |

(23) P(62-68):
BOC—Ser(Bzl)—His—Glu(OBzl)—Lys(Z—Cl-)—Ser(Bzl)—Leu—Gly—OH [23]

A dioxane solution (52 ml) of 4.32 N HCl and isoamylnitrile (20 ml) were added to substance [22] (33.5 g) dissolved in DMF (200 ml) at −50° C., and the mixture was stirred at −20° C. for 10 minutes. $Et_3N$ (31.6 ml) was added at −50° C.

Methylene chloride (20 ml) was added to substance [21] (63.85 g, 64 mM). TFA (200 ml) was added thereto at 5° C. and the mixture was stirred at room temperature for 50 minutes. The TFA was distilled off in vacuo, ether was added to the residual oily substance and the thus-formed precipitate was collected and was dissolved in DMF (200 ml), then neutralized with NMM at 5° C.

The neutralized DMF solution was added to the above triethylamine-treated solution and stirred with refrigeration overnight and then at room temperature overnight. The DMF was removed in vacuo and the residue was dissolved in methanol. The solution was poured into water, then the precipitate formed was washed with water and dried. The resulting material was recrystallized from DMF-ether, and washed twice with methanol to obtain substance [23] (59.16 g, yield: 60.1%).
m.p.: 209°-213° C. (decomp.)
TLC: $Rf_4=0.66$

| Elementary analysis [$C_{65}H_{83}O_{17}N_{10}Cl$]: | C % | H % | N % |
|---|---|---|---|
| Found | 59.43 | 6.58 | 10.67 |
| Calculated | 59.51 | 6.38 | 10.68 |

Amino acid analysis [1.549 mg/0.5 ml 6 N HCl, 105° C., 21 hours]: Ser 1.82 (2), Glu 1.01 (1), Gly 0.98 (1), Leu 1, Lys 1.01 (1), His 0.94 (1).

(24) P(62-84):
BOC—Ser(Bzl)—His—Glu(OBzl)—Lys(Z—Cl-)—Ser(Bzl)—Leu—Gly—Glu(OBzl)—Ala—Asp(OBzl)—Lys(Z—Cl)—Ala—Asp(OBzl)—Val—Asp(OBzl)—Val—Leu—Thr(Bzl)—Lys(Z—Cl)—Ala—Lys(-Z—Cl)—Ser(Bzl)—Gln—OBzl [24]

TFA (250 ml) was added to substance [17] (75.35 g, 25.5 mM) and the mixture was stirred at room temperature for 60 minutes. The TFA was removed in vacuo and ether was added to the residue. The precipitate was collected and dissolved in NMP (500 ml) and DMF (500 ml). The reaction mixture was poured into ice and 5% sodium bicarbonate, and the precipitate was collected and washed with water and methanol. The precipitate was dissolved in NMP (1 lit.) and DMF (1 lit.), 2,4-dinitrophenol (5.61 g, 1.2 molar excess), HOBT (4.08 g, 1.2 molar excess), substance [23] (40.16 g, 1.2 molar excess) and WSCI (5.6 ml, 1.2 molar excess) were added thereto and stirred at room temperature for four days. The reaction mixture was poured into 5% sodium bicarbonate-ice, and the precipitate was collected, which was washed with water, hot methanol and twice with methanol to obtain substance [24] (93.53 g, yield: 88.4%). Amino acid analysis: Asp 2.67 (3), Thr 0.81 (1), Ser 1.37 (3), Glu 2.59 (3), Gly 0.76 (1), Ala 2.68 (3), Val 2, Leu 1.74 (2), Lys 3.66 (4), His 0.66 (1).

(25) P(61-84):
BOC—Glu(OBzl)—Ser(Bzl)—His—Glu(OBzl)—Lys(Z—Cl)—Ser(Bzl)—Leu—Gly—Glu(OBzl)—Ala—Asp(OBzl)—Lys(Z—Cl)—Ala—Asp(OBzl)—Val—Asp(OBzl)—Val—Leu—Thr(Bzl)—Lys(Z—Cl)—Ala—Lys(Z—Cl)—Ser(Bzl)—Gln—OBzl [25]

TFA (150 ml) was added to substance [24] (41.5 g, 10 mM); the mixture was stirred at room temperature for 60 minutes, and the TFA was removed in vacuo. Ether was added to the residue, and the precipitate was collected which was dissolved in DMF (300 ml) and NMP (500 ml). The solution was poured into 5% sodium bicarbonate-ice, and the precipitate was collected and washed with water and methanol. DMF (700 ml) and NMP (600 ml) were added to dissolve the precipitate. 2,4-dinitrophenol (2.2 g, 1.2 molar excess), BOC—Glu(OBzl)—OSU (6.08 g, 1.4 molar excess), HOBT (0.23 g, 0.14 molar excess) and NMM (1.52 ml, 1.4 molar excess) were added and the mixture was stirred at room temperature overnight. BOC—Glu(OBzl)—OSU (0.87 g, 9.2 molar excess) and NMM (0.22 ml, 0.2 molar excess) were added and further stirred overnight. The reaction mixture was poured into ice and 5% sodium bicarbonate, and the precipitate was collected and was washed with water and methanol, DMF (700 ml) and NMP (600 ml) were added to dissolve the precipitate. 2,4-dinitrophenol (2.2 g, 1.02 molar excess), BOC—Glu(OBzl)—OSU (6.08 g, 1.4 molar excess), HOBT (0.23 g, 0.14 molar excess) and NMM (1.52 ml, 1.4 molar excess) were added thereto and stirred at room temperature overnight. BOC—Glu(OBzl)—OSU (0.87 g, 0.2 molar excess) and NMM (0.22 ml, 0.2 molar excess) were further added to the reaction mixture and stirred overnight. The reaction mixture was poured into ice and 5% sodium bicarbonate, and the precipitate was collected, washed completely with water, then washed three times with hot methanol to obtain substance [25] (4.07 g, yield: 93.2%).

Amino acid analysis [6 N HCl/anisole, 110° C., 48 hours]: Asp 2.66 (3), Thr 0.85 (1), Ser 1.56 (3), Glu 3.14 (4), Gly 0.71 (1), Ala 2.65 (3), Val 2, Leu 1.73 (2), Lys 3.67 (4), His 0.63 (1).

(26) P(59-60): BOC—Leu—Val—OBzl [26]

Ethyl acetate (100 ml) was added to H—Val—OBzl-.TosoH (17.8 g, 47 mM), and the mixture was washed with 5% sodium bicarbonate and water, dried with anhydrous sodium sulfate and the ethyl acetate was removed in vacuo. The residue was dissolved in DMF (100 ml). BOC—Leu—OH.$H_2O$ (11.7 g, 56.4 mM), HOBT (9.3 g, 1.2 molar excess) and WSCI (10.3 ml, 1.3 molar excess) were added and the mixture was stirred at room temperature overnight. The DMF was removed in vacuo, and the residue was dissolved in ethyl acetate (300 ml) and washed with 5% sodium bicarbonate, 1 N NCl and water. After drying with anhydrous sodium sulfate, the solution was dried in vacuo. The residue was recrystallized from ethyl acetate-hexane to obtain substance [26] (17.55 g, yield: 88.8%).

TLC: $Rf_4=0.85$

(27) P(58-60): BOC—Val—Leu—Val—OBzl [27]

TFA (50 ml) was added to substance [26] (17.2 g, 41 mM), the mixture was stirred at room temperature and the TFA was removed. Ether was added to the residue, and the precipitate was collected which was dissolved in DMF (300 ml). HOBT (7.7 g, 1.2 molar excess), BOC—VAl—OH (1.07 g, 1.2 molar excess), and WSCI 9.0 ml, 1.2 molar excess) were added thereto, and the pH was adjusted to 7 by adding NMM; then the mixture was stirred at room temperature overnight. The DMF was removed in vacuo, and the residue was dissolved in ethyl acetate (300 ml) and washed with 5% sodium bicarbonate, 1 N HCl and water. The solution was dried with anhydrous sodium sulfate and dried in vacuo. The residue was recrystallized twice from ethyl acetate-hexane to obtain substance [27] (17.38 g, yield: 81.6%).

m.p.: 149°-152° C.

TLC: $Rf_5=0.82$ $[a]_D^{22}=-32.3$ 6(c=1.0, DMF)

| Elementary analysis [$C_{28}H_{45}O_6N_3$]: | C % | H % | N % |
|---|---|---|---|
| Found | 64.80 | 8.81 | 8.20 |
| Calculated | 64.71 | 8.73 | 8.09 |

(28) P(57-60): BOC—Asn—VAl—Leu—Val—OBzl [28]

TFA (50 ml) was added to substance [27] (17.15 g, 33 mM), the mixture was stirred at room temperature for 25 minutes, and the TFA was removed in vacuo. Ether was added to the residue, the precipitate was collected and dissolved in DMF (100 ml). HOBT (0.62 g, 0.14 molar excess), and BOC—Asn—ONP (16.32 g, 1.4 molar excess) were added thereto, and the pH was adjusted to 7 by adding NMM; then the mixture was stirred at room temperature for two days. The DMF was removed in vacuo, and the residue was poured into 5% sodium bicarbonate and ice. The precipitate was dissolved in chloroform and washed with 5% sodium bicarbonate and water. The solution was dried with anhydrous sodium sulfate and dried in vacuo. The residue was recrystallized twice from ethanol-ether to obtain substance [28] (13.82 g, yield: 79.5%).

TLC: $Rf_2=0.70$

| Elementary analysis [$C_{32}H_{51}O_8N_5$]: | C % | H % | N % |
|---|---|---|---|
| Found | 60.83 | 8.19 | 11.09 |
| Calculated | 60.64 | 3.11 | 11.05 |

(29) P(57-60): BOC—Ans—VAl—Leu—Val—OH [29]

Substance [28] (13.2 g, 25 mM) was dissolved in ethanol (50 ml) and DMF (60 ml). 5% Pd/C (1 g) was added thereto and the material was hydrogenated for 3 hours.

The catalyst was filtered off and the filtrate was concentrated in vacuo. The residue was recrystallized twice from ethanol-ether to obtain substance [29] (9.70 g, yield: 71.4%).

TLC: $Rf_2=0.56$

Amino acid analysis: Asp 1.02 (1), Val 1.95 (2), Leu 1 (1).

| Elementary analysis [$C_{25}H_{45}O_{11}N_5$]: | C % | H % | N % |
|---|---|---|---|
| Found | 55.02 | 8.13 | 13.06 |
| Calculated | 55.23 | 8.34 | 12.88 |

(30) P(57-84):

BOC—Asn—Val—Leu—Val—Glu(OBzl)—Ser(Bzl)—His—Glu(OBzl)—Lys(Z—Cl)—Ser(Bzl)—Leu—Gly—Glu(OBzl)—Ala—Asp(OBzl)—Lys(Z—Cl)—Ala—Asp(OBzl)—Val—Asp(OBzl)—Val—Leu—Thr(Bzl)—Lys(Z—Cl)—Ala—Lys(Z—Cl)—Ser(Bzl)—Gln—OBzl [30]

TFA (150 ml) was added to substance [25] (39.75 g, 9.1 mM) and the mixture was stirred at room temperature for 60 minutes. The TFA was removed in vacuo and ether was added to the residue. The precipitate was collected and was dissolved in DMF (600 ml) and NMP (600 ml). The reaction mixture was poured into ice and 5% sodium bicarbonate, and the precipitate was filtered off and then washed three times with water and once with methanol. NMP (1.2 lit.) and DMF (1.2 lit.) were added to dissolve the precipitate. HOBT (1.60 g, 1.3 molar excess), 2,4-dinitrophenol (2.18 g, 1.3 molar excess), substance [29] (6.43 g, 1.3 molar excess) and WSCI (4.32 ml, 2.6 molar excess) were added thereto, and the mixture was stirred at room temperature for two days. Further substance [29] (0.99 g, (0.2 molar excess) dissolved in DMF (100 ml) was added thereto, and the mixture was stirred at room temperature overnight. The reaction mixture was poured into 5% sodium bicarbonate and ice, and the precipitate was collected and suspended in DMF (100 ml) and heated. After cooling the mixture, the insolubles were filtered off. Then the insolubles were treated with methanol and ethanol while heating, in the same way as the above, to obtain substance [30] (42.25 g, yield: 97.2%).

Amino acid analysis: Asp 3.34 (4), Thr 0.93 (1), Ser 1.60 (3), Glu 3.24 (4), Gly 0.85 (1), Ala 3, Val 3.39 (4), Leu 2.58 (3), Lys 4.24 (4), His 0.79 (1).

(31) P(56-84):

BOC—Asp(OBzl)—Asn—Val—Leu—Val—Glu(OBzl)—Ser(Bzl)—His—Glu(OBzl)—Lys(Z—Cl)—Ser(Bzl)—Leu—Gly—Glu(OBzl)—Ala—Asp(OBzl)—Lys(Z—Cl)—Ala—Asp(OBzl)—Val—Asp(OBzl)—Val—Leu—Thr(Bzl)—Lys(Z—Cl)—Ala—Lys(Z—Cl)—Ser(Bzl)—Gln—OBzl [31]

TFA (150 ml) was added to substance [30] (28.7 g, 6 mM) and the mixture was stirred at room temperature for 50 minutes. The TFA was removed in vacuo and ether was added to the residue. The precipitate was collected and dried over NaOH overnight. The precipitate was dissolved in DMF (300 ml) and HMP (500 ml). HOBT (0.16 g, 0.2 molar excess) and BOC—Asp(OBzl)—OSU (5.04 g, 2 molar excess) were added, and the mixture was adjusted to pH 7.0 by adding NMM and was stirred at room temperature overnight. Further BOC—Asp(OBzl)—OSU (2.50 g, equimolar) was added and the mixture was stirred overnight. The reaction mixture was poured into ice water; and the precipitate was collected, washed with water, then heated in methanol. After cooling, the insoluble material was filtered off. The heating in methanol was repeated three times to obtain substance [31] (27.75 g, yield: 92.5%).

Amino acid analysis: Asp 4.00 (5), Thr 0.92 (1), Ser 1.69 (3), Glu 3.57 (4), Gly 0.81 (1), Ala 3, Val 3.22 (4), Leu 2.62 (3), Lys 4.12 (4), His 0.62 (1).

(32) P(55-84):

BOC—Glu(OBzl)—Asp(OBzl)—Asn—Val—Leu—Val—Glu(OBzl)—Ser(Bzl)—His—Glu(OBzl)—Lys(Z—Cl)—Ser(Bzl)—Leu—Gly—Glu(OBzl)—Ala—Asp(OBzl)—Lys(Z—Cl)—Ala—Asp(OBzl)—Val—Asp(OBzl)—Val—Leu—Thr(Bzl)—Lys(Z—Cl)—Ala—Lys(Z—Cl)—Ser(Bzl)—Gln—OBzl [32]

TFA (150 ml) was added to substance [31] (27.50 g, 5.5 mM) and the mixture was stirred at room temperature for 50 minutes. The TFA was removed in vacuo, ether was added to the residue, and the precipitate was collected and dried over NaOH for two days. The precipitate was dissolved in DMF (300 ml) and NMP (500 ml). 2,4-dinitrophenol (1.01 g, equimolar amount), HOBT (0.11 g, 0.15 molar excess) and BOC—Glu(OBzl)—OSU (3.10 g, 1.3 molar excess) were added thereto, and the mixture was stirred at room temperature overnight. Further BOC—Glu(OBzl)—OSU (3.10 g, 1.3 molar excess) was added and the mixture was stirred for two days. The reaction mixture was poured into ice and 5% sodium bicarbonate. The precipitate was washed twice with 5% sodium bicarbonate and three times with water. Methanol was added to the precipitate, which was heated, and after cooling, the insolubles were filtered off. The heating and filtration were repeated three times to obtain substance [32] (26.77 g, yield: 93.3%).

Amino acid analysis: Asp 4.11 (5), Thr 0.92 (1), Ser 1.59 (3), Glu 3.99 (5), Gly 0.83 (1), Ala 3, Val 3.28 (4), Leu 2.49 (3), Lys 4.08 (4), His 0.71 (1).

(33) P(53-54): Boc—Lys(Z—Cl)—Lys(Z—Cl)—PAC [33]

BOC—Lys(Z—Cl)—OH.TBA (36.6 g, 75 mM) was suspended in ethyl acetate (300 ml) and washed with ice-cold 1 N HCl and water. The ethyl acetate layer was dried with anhydrous sodium sulfate, dried in vacuo, and dissolved in DMF (50 ml). Phenacylbromide (19.40 g) and $Et_3N$ (13.60 ml, 1.3 molar excess) were added thereto and the mixture was stirred at room temperature for four hours. Sodium acetate (3.68 g, 0.5 molar excess) dissolved in ethyl acetate (500 ml) was added to the reaction mixture, which was then washed three times with 5% sodium bicarbonate, 1 N HCl and water, respectively. After drying the ethyl acetate layer with anhydrous sodium sulfate, the material was dried in vacuo. The residue was purified by silica-gel column chromatography [developer: benzene-ethyl acetate (2:1)], and the fractions showing $Rf_1=0.77$ on TLC were collected and dried in vacuo. The residue was recrystallized from ether-hexane to obtain BOC—Lys(Z—Cl)—PAC (23.46 g, yield: 60.5%).

m.p.: 52°-54° C.

TLC: $Rf_1=0.86$

TFA (60 ml) was added to the above product (20.68 g, 40 mM) and the mixture was stirred at room temperature for 20 minutes. The TFA was removed in vacuo, ether was added to the residue, and the precipitate was collected and dissolved in DMF (50 ml). (This solution is hereinafter designated as DMF solution A).

BOC—Lys(Z—Cl)—OH.TBA (23.42 g, 1.2 molar excess) suspended in ethyl acetate (200 ml) was washed with ice and 1 N HCl (200 ml) and water (100 ml). After drying the ethyl acetate layer with anhydrous sodium sulfate, the material was dried in vacuo. The thus-obtained oily material was dissolved in DMF (50 ml). (This solution is hereinafter designated as DMF solution B).

DMF solution B, HOBT (6.48 g, 1.2 molar excess) and WSCI (8.78 ml, 1.2 molar excess) were added to the DMF solution A, which was then adjusted to pH 7 by adding NMM and stirred at room temperature overnight. The DMF was removed in vacuo, and the residue was dissolved in ether (500 ml), and washed three times with 5% sodium bicarbonate. Ethyl acetate (300 ml) was added to the ether layer, which was then washed twice with 1 N HCl and three times with water. The organic layer was dried with adhydrous sodium sulfate and concentrated in vacuo. The residue was recrystallized three times from ether to obtain substance [33] (18.73 g, yield 57.5%).

m.p.: 72°-75° C.

| Elementary analysis [$C_{41}H_{50}O_{10}N_4Cl_2$]: | | | |
|---|---|---|---|
| | C % | H % | N % |
| Found | 59.22 | 5.98 | 6.81 |
| Calculated | 59.35 | 6.07 | 6.75 |

(34) P(53-54): BOC—Lys(Z—Cl)—Lys(Z—Cl)—OH [34]

Substance [33] (4.07 g, 5 mM) was dissolved in acetic acid (30 ml). Zinc powder (20 g)/acetic acid (30 ml) was added and the mixture was stirred at room temperature for 1.5 hours. The zinc powder was removed by filtration and the filtrate was concentrated in vacuo to remove the acetic acid. The residue was dissolved in ether (100 ml) and extracted three times with 5% sodium bicarbonate (70 ml). The aqueous layer was adjusted to pH 2 by adding 1 N HCl with ice cooling. Then the mixture was extracted with ethyl acetate. The ethyl acetate layer was washed with water, dried with anhydrous sodium sulfate and dried in vacuo. The residue was recrystallized from ether-hexane to obtain substance [34] (3.08 g, yield: 85.8%).

m.p.: 59°-62° C.

TLC: $Rf_2=0.45$

| Elementary analysis [$C_{33}H_{44}O_9N_4Cl_2$]: | | | |
|---|---|---|---|
| | C % | H % | N % |
| Found | 55.58 | 6.40 | 7.58 |
| Calculated | 55.69 | 6.23 | 7.87 |

(35) P(53-84):
BOC—Lys(Z—Cl)—Lys(Z—Cl)—Glu(OBzl)—Asp(OBzl)—Asn—Val—Leu—Val—Glu(OBzl)—Ser(Bzl)—His—Glu(OBzl)—Lys(Z—Cl)—Ser(Bzl)—Leu—Gly—Glu(OBzl)—Ala—Asp(OBzl)—Lys(Z—Cl)—Ala—Asp(OBzl)—Val—Asp(OBzl)—Val—Leu—Thr(Bzl)—Lys(Z—Cl)—Ala—Lys(Z—Cl)—Ser(Bzl)—Gln—OBzl [35]

TFA (50 ml) was added to substance [32] (7.83 g, 1.5 mM) and the mixture was stirred at room temperature for 55 minutes. The TFA was removed in vacuo, and ether was added to the residue. The precipitate was collected and was dissolved in DMF (150 ml) and NMP (150 ml). HOBT (0.41 g, 2.0 molar excess), substance [34] (2.13 g, 2.0 molar excess) and WSCI (0.55 ml, 2.0 molar excess) were added thereto, and the mixture was stirred at 5°-10° C. for 3 days. The reaction mixture was poured into ice water, and the precipitate was collected, washed with water and heated with methanol. After cooling, the insolubles were collected by filtration. This heat treatment was repeated three times to obtain substance [35] (8.31 g, yield: 95.3%).

Amino acid analysis: Thr 0.92 (1), Ser 1.60 (3), Glu 4.06 (5), Gly 0.85 (1), Ala 3.00 (3), Val 3.33 (4), Leu 2.48 (3), Lys 5.41 (6), His 0.70 (1).

(36) h-PTH [53-84]

(a) Substance [35] (3.49 g, 0.6 mM) and anisole (3 ml) were added to anhydrous HF (25 ml) at 0° C. and stirred for 75 minutes. After reaction, the HF was removed in vacuo, and ether was added to the residue. The thus-formed precipitate was collected, dissolved in 0.1 N acetic acid (50 ml) and passed through a Dowex X1 column (2.7×35 cm). The eluate was lyophilized to obtain a crude product (2.18 g). This was dissolved in 8 M urea solution (50 ml), and the solution was adjusted to pH 9.5 by adding aqueous ammonina, and allowed to stand for 50 minutes. The solution was charged on a column (4.4×12 cm) of CM-cellulose packed with 8 M urea solution, which was eluted with 0.01 M ammonium acetate (pH 4.5, about 100 ml) and eluted by linear gradient elution with 0.01 M ammonium acetate (pH 4.5, 700 ml)-0.1 M ammonium acetate (pH 4.5, 700 ml), then eluted with 0.2 M ammonium acetate (pH 4.5, 300 ml). The eluate was fractionated into fractions of 13.5 ml each. Each fraction was checked by the Folin-Lowry method (500 nm). Fractions Nos 30-50 (fraction $C_1$), fractions Nos. 56-119 (fraction $C_2$) and fractions Nos. 120-150 (fraction $C_3$) were obtained.

Each of fractions $C_1$-$C_3$ was desalted by passing it through a Sephadex LH-20 column. The eluate was fractionated into fractions each 8.5 ml, whose activities were checked the same way as above. Fraction $C_1$ was passed through the column (3.4×113 cm) to obtain fractions Nos. 31-40 (fraction $L_1$; fractions Nos. 41-44 (fraction $L_2$); and fractions Nos. 45-54 (fraction $L_3$).

Fraction $C_2$ was passed through such a column (3.4×120 cm) to obtain fractions Nos. 34-45 (fraction $L_1$); fractions Nos. 46-52 (fraction $L_2$); and fractions Nos. 53-60 (fraction $L_3$).

Fraction $C_3$ was passed through such a column (3.4×120 cm) to obtain fractions Nos. 31-44 (fraction $L_1$); fractions Nos. 45-52 (fraction $L_2$). Each of the fractions was lyophilized to obtain the components shown in the following Table 1.

(b) Purification of $C_2L_2$:

$C_2L_2$ (565 mg) dissolved in 0.1 N acetic acid (5 ml) was charged on a column (4.4×70 cm) of CM-cellulose, which was eluted with a linear gradient elution of 0.01 M ammonium acetate solution (pH 4.5, 500 ml)-0.1 M ammonium acetate solution (pH 4.5, 500 ml). The eluate was fractionated into fractions of 6.0 ml each, and each fraction was checked by the Folin-Lowry method to obtain fractions Nos. 113-136 (fraction $C_2L_2$-$C_1$), fractions Nos. 137-151 (fraction $C_2L_2$-$C_2$) and fractions Nos. 152-190 (fraction $C_2L_2$-$C_3$).

TABLE 1

| components | | Amino acid analysis | | | | | | | | | |
|---|---|---|---|---|---|---|---|---|---|---|---|
| fractions | yield: (mg) | Asp (5) | Thr (1) | Ser (3) | Glu (5) | Gly (1) | Ala (3) | Val (4) | Leu (2) | Lys (6) | His (1) |
| $C_1L_1$ | 182 | 3.81 | 1.12 | 2.06 | 3.21 | 0.63 | 3 | 3.04 | 2.15 | 4.21 | 0.46 |
| $C_1L_2$ | 353 | 3.79 | 1.01 | 2.07 | 3.71 | 0.79 | 3 | 3.09 | 2.35 | 4.45 | 0.66 |
| $C_1L_3$ | 304 | 3.31 | 1.01 | 1.70 | 2.94 | 0.55 | 3 | 2.74 | 1.96 | 4.11 | 0.43 |
| $C_2L_1$ | 166 | 4.26 | 1.00 | 2.28 | 4.44 | 0.96 | 3 | 3.57 | 2.80 | 5.67 | 0.87 |
| $C_2L_2$ | 568 | 4.76 | 0.97 | 2.33 | 4.80 | 0.96 | 3 | 3.88 | 2.93 | 5.89 | 0.87 |
| $C_3L_3$ | 120 | 4.19 | 1.04 | 2.03 | 4.02 | 0.82 | 3 | 3.44 | 2.56 | 4.97 | 0.66 |
| $C_3L_1$ | 170 | 4.55 | 1.02 | 2.29 | 4.65 | 1.03 | 3 | 3.82 | 2.95 | 6.00 | 0.83 |
| $C_3L_2$ | 157 | 4.58 | 0.96 | 2.36 | 4.69 | 1.09 | 3 | 3.81 | 3.00 | 6.49 | 0.95 |

Each of these fractions was passed through Sephadex LH-20 for desalting. The eluates were fractionated into fractions of 5.2 ml each, and each fraction was chcked by the same method as above. Fraction $C_2L_2$-$C_1$ was passed through such a column (3.4×120 cm) to obtain fractions Nos. 55-72 (fraction $C_2L_2$-$C_1L_1$) and fractions Nos. 73-80 (fraction $C_2L_2$-$C_1L_2$). Fraction $C_2L_2$-$C_2$ was passed through such a column (3.4×110 cm) to obtain fractions Nos. 50-59 (fraction $C_2L_2$-$C_2L_1$) and fractions Nos. 60-67 (fraction $C_2L_2$-$C_2L_2$). Fraction $C_2L_2$-$C_3$ was passed through such a column (3.4×110 cm) to obtain fraction Nos. 45-60 (fraction $C_2L_2$-$C_3L_1$) and fractions Nos. 61-72 (fraction $C_2L_2$-$C_3L_2$). Each fraction was lyophilized to obtain the following components:

| | |
|---|---|
| $C_2L_2$-$C_1L_1$ | 106.7 mg |
| $C_2L_2$-$C_1L_2$ | 95.9 mg |
| $C_2L_2$-$C_2L_1$ | 53.6 mg |
| $C_2L_2$-$C_2L_2$ | 44.1 mg |
| $C_2L_2$-$C_3L_1$ | 97.0 mg |
| $C_2L_2$-$C_3L_2$ | 95.1 mg |

Purification of $C_2L_2$-$C_1L_1$:

The above $C_2L_2$-$C_1L_1$ dissolved in 0.1 N acetic acid was charged on a column (2.0×15 cm) of CM-cellulose, and eluted by linear gradient elution with 0.01 M ammonium acetate (pH 4.5, 300 ml)—0.1 M ammonium acetate (pH 4.5, 300 ml). The elutes were fractionated into fractions of 7.4 ml each, and each fraction was checked by the Folin-Lowry method (500 nm) to obtain fractions Nos. 46-56 (fraction $C_2L_2$-$C_1L_1$-C). This fraction was concentrated in vacuo and charged on a column (3.0×90 cm) of Sephadex LH-20 and eluted with 0.1 N acetic acid. The eluate was fractionated into fractions of 6.0 ml each. The fractions were checked by the same method as hereinabove to obtain fractions Nos. 25-35 (fraction $C_2L_2$-$C_1L_1$-CL), which was lyophilized to obtain h-PTH [53-84] (90.0 mg).

TLC: $R_9$=0.76 (one spot)

Amino acid analysis: Asp 4.45 (5), Thr 0.92 (1), Ser 2.16 (3), Glu 4.94 (5), gly 0.96 (1), Ala 3, Val 3.96 (4), Leu 2.92 (3), Lys 6.22 (6), His 1.01 (1).

EXAMPLE 2

H—Pth(51-84);
H—Pro—Arg—Lys—Lys—Glu—Asp—Asn—Val—Leu—Val—Glu—Ser—His—Glu—Lys—Ser—Leu—Gly—Glu—Ala—Asp—Lys—Ala—Asp—Val—Asp—Val—Leu—Thr—Lys—Ala—Lys—Ser—Gln—Oh (1) P(51-84):
BOC—Pro—Arg(Tos)—Lys(Z—cl)—Lys(Z—Cl)—Glu(OBzl)—Asp(OBzl)—Asn—Val—Leu—Val—glu(OBzl)—Ser(Bzl)—His—Glu(OBzl)—Lys(Z—Cl)—Ser(Bzl)—Leu—Gly—Glu(OBzl)—Ala—Asp(OBzl)—Lys(Z—Cl)—Ala—Asp(OBzl)—Val—Asp(OBzl)—Val—Leu—Thr(Bzl)—Lys(Z—Cl)—Ala—Lys(Z—Cl)—Ser(Bzl)—Gln—OBzl [39]

TFA (50 ml) was added to substance [32] (7.82 g, 1.5 mM) obtained in Example 1, and the mixture was stirred at room temperature for 60 minutes. The TFA was removed in vacuo and ether was added to the residue. The precipitate was collected and was dissolved in DMF (120 ml) and NMP (120 ml). HOBT (0.30 g, 1.5 molar excess), a substance (2.52 g, 1.5 molar excess) of the formula BOC—Pro—Arg(Tos)—Lys(Z—Cl)—Lys(Z—Cl)—OH and WSCI (0.41 ml, 1.5 molar excess) were added thereto, the the mixture was stirred at room temperature for two days. The reaction mixture was poured into ice water. The thus-formed precipitate was washed with water and methanol was added to the precipitate and the mixture was heated. After cooling, the insolubles were collected by filtration. The above heating, cooling and filtration operations were twice repeated, and the product was washed with ether to obtain substance [39] (8.20 g, yield: 87.9%).

Amino acid analysis: Asp 4.09 (5), Thr 1.05 (1), Ser 2.30 (3), Glu 4.08 (5), Pro 0.52 (1), Gly 0.83 (1), Ala 3, Val 3.42 (4), Leu 2.53 (3), Lys 5.11 (6), His 0.69 (1), Arg 0.51 (1).

(2) h-PTH [51-84]

Substance [39] (3.73 g, 0.6 mM) and anisole (4 ml) were added to anhydrous HF (40 ml) at 0° C. and the mixture was stirred for 60 mins. The HF was distilled off in vacuo, and ether was added to the residue. The precipitate was collected and passed through a column of Dowex X1 (acetate form, 2.7×33 cm) after dissolved in acetic acid (50 ml). The eluate was lyophilized to obtain a crude product (2.18 g).

This was dissolved in 8 M urea (50 ml), and the solution was adjusted to pH 10.0 by adding aqueous ammonia, then allowed to stand for 30 minutes. The solution was charged on a column (4.2×11.5 cm) of CM-cellulose packed with 8 M aqueous urea, and the urea was removed by adding 0.01 M ammonium acetate (pH 4.5). Then the column was eluted by linear gradient elution of 0.01 M ammonium acetate (pH 4.5, 700 ml)—0.1 M ammonium acetate (pH 4.5, 700 ml), and eluted with 0.2 M ammonium acetate (pH 4.5, 250 ml). The eluate was fractionated into fractions each 8.5 ml and each fraction was checked by the Folin-Lowry method (500 nm) to obtain fractions Nos 30-63 (fraction $C_1$), the fractions Nos. 105-150 (fraction $C_2$) and fractions Nos. 151-195

(fraction $C_3$). The fractions $C_2$ and $C_3$ were passed through Sephadex LH-20 for desalting. The eluate was fractionated into fractions of 5.2 ml each. The fraction $C_2$ was passed through a column (3.4×120 cm) to obtain fractions Nos. 51-63 (fraction $C_2L_1$) and fractions Nos. 64-80 (fraction $C_2L_2$). The fraction $C_3$ was passed through such a column (3.4×120 cm) to obtain fractions Nos. 50-69 (fraction $C_3L_1$) and fractions Nos. 70-78 (fraction $C_3L_2$). Each fraction was lyophilized to obtain the components shown in the following Table 2.

The above fraction $C_2L_2$ (375 mg) dissolved in 0.1 N acetic acid (4 ml) was charged on a column (2.0×31 cm) of CM-cellulose and eluted by linear gradient elution with 0.01 M ammonium acetate (pH 4.5, 500 ml)—0.1 M ammonium acetate (pH 4.5, 300 ml). The eluate was fractionated into fractions of 7.5 ml each, and fractions Nos. 85-130 (fraction $C_2L_2$-C) were obtained. This was passed through a column of Sephadex LH-20 (3.0×123 cm) for desalting. The eluate was fractionated into 6 ml fractions to obtain fractions Nos. 34-42 (fraction $C_2L_2$-$CL_1$) and fractions Nos. 43-50 (fraction $C_2L_2$-$CL_2$). Each fraction was lyophilized to obtain the following fractions:

$C_2L_2$-$CL_1$: 80.0 mg

Amino acid analysis: Asp 4.95 (5), Thr 0.98 (1), Ser 2.47 (3), Glu 5.14 (5), Gly 1.01 (1), Ala 3 (3), Val 4.05 (4), Leu 3.02 (3), Lys 6.16 (6), His 0.96 (1), Arg 0.97 (1), Pro 1.06 (1).

$C_2L_2$-$CL_2$: 197.6 mg

Amino acid analysis: Asp 5.00 (5), Thr 0.93 (1), Ser 2.30 (3), Glu 5.17 (5), Gly 1.01 (1), Ala 3 (1), Val 4.03 (4), Leu 3.00 (3), Lys 6.15 (6), His 0.95 (1), Arg 1.01 (1), Pro 1.04 (1).

Fraction $C_2L_2$-$CL_2$ (195 mg) hereinabove, dissolved in 0.1 N acetic acid (2 ml), was charged on a column (2.0×15 cm) of CM-cellulose and eluted by linear gradient elution with 0.01 M ammonium acetate (pH 4.5, 300 ml)—0.2 M ammonium acetate (pH 4.5, 300 ml). The eluate was fractionated into 6.4 ml fractions to obtain fractions Nos. 55-64 (fraction $C_2L_2$-$CL_2$-$C_1$) and fractions Nos. 66-72 (fraction $C_2L_2$-$CL_2$-$C_2$). Each fraction was passed through Sephadex LH-20 for desalting. Fraction $C_2L_2$-$Cl_2$-$C_1$ was passed through a column (3.0×123 cm) and the eluate was fractionated into 7.4 ml fractions to obtain fractions Nos. 31-38 (fraction $C_2L_2$-$CL_2$-$C_1L_1$) and fractions Nos. 39-43 (fraction $C_2L_2$-$CL_2$-$C_1L_2$). Fraction $C_2L_2$-$CL_2$-$C_1L_1$ was lyophilized to obtain h-PTH [53-84] (77.2 mg).

TLC: $R_{10}$=0.89 (one spot)

TABLE 2

| component | | amino acid analysis | | | | | | | | | | | |
|---|---|---|---|---|---|---|---|---|---|---|---|---|---|
| fractions | yield mg. | Asp (5) | Thr (1) | Ser (3) | Glu (5) | Gly (1) | Ala (3) | Val (4) | Leu (3) | Lys (6) | His (1) | Arg (1) | Pro (1) |
| $C_2L_1$ | 100 | 4.38 | 1.07 | 2.18 | 4.28 | 0.84 | 3 | 3.65 | 2.65 | 5.23 | 0.69 | 0.56 | 0.59 |
| $C_2L_2$ | 378 | 4.78 | 0.95 | 2.30 | 5.02 | 0.99 | 3 | 3.95 | 2.98 | 5.97 | 0.89 | 0.96 | 0.99 |
| $C_3L_1$ | 196 | 4.45 | 1.06 | 2.24 | 4.52 | 0.94 | 3 | 3.75 | 3.01 | 5.63 | 0.77 | 0.71 | 0.76 |
| $C_3L_2$ | 458 | 4.70 | 0.93 | 2.31 | 4.92 | 1.03 | 3 | 3.89 | 2.94 | 6.05 | 0.93 | 0.99 | 1.00 |

EXAMPLE 3

H—PTH (46-48):

H—Ala—Gly—Ser—Gln—Arg—Pro—Arg—Lys—Lys—Glu—Asp—Asn—Val—Leu—Val—Glu—Ser—His—Glu—Lys—Ser—Leu—Gly—Glu—Ala—Asp—Lys—Ala—Asp—Val—Asp—Val—Leu—Thr—Lys—Ala—Lys—Ser—Gln—Oh (1) P (46-84):

BOC—Ala—Gly—Ser(Bzl)—Gln—Arg(Tos)—Pro—Arg(Tos)—Lys(Z—Cl)—Lys(Z—Cl)—Glu(OBzl)—Asp(OBzl)—Asn—Val—Leu—Val—Glu(OBzl)—Ser(Bzl)—His—Glu(OBzl)—Lys(Z—Cl)—Ser(Bzl)—Leu—Gly—Glu(OBzl)—Ala—Asp(OBzl)—Lys(Z—Cl)—Ala—Asp(OBzl)—Val—Asp(OBzl)—Val—Leu—Thr(Bzl)—Lys(Z—Cl)—Ala—Lys(Z—Cl)—Ser(Bzl)—Gln—OBzl [46]

TFA (80 ml) was added to substance [32] in Example 1 (10.44 g, 2 mM) and the mixture was stirred at room temperature for 60 minutes. The TFA was removed in vacuo and ether was added to the residue to form a precipitate which was dissolved in DMF (160 ml) and NMP (160 ml). A substance (4.28 g, 1.15 molar excess) of the formula BOC—Ala—Gly—Ser(Bzl)—Gln—Arg(Tos)—Pro—Arg(Tos)—Lys(Z—Cl)—Lys(Z—Cl)—OH, HOBT (0.32 g, 1.2 molar excess) and WSCI (0.44 ml, 1.2 molar excess) were added thereeto, and the mixture was stirred at room temperature for two days. The DMF was removed in vacuo. Ice water was added to the residue and the precipitate was filtered off and was heated after adding methanol (200 ml). After cooling, the insolubles were collected. This operation was repeated twice to obtain substance [46] (12.17 g, yield: 87.4%).

(2) h-PTH [46-84]

The substance [46] (4.18 g, 0.6 mM) and anisole (10 ml) were added to HF (60 ml) at 0° C. and the mixture was stirred for 60 mins. After reaction, the HF was distilled off in vacuo and ether was added to the residue. The precipitate was collected, dissolved in 10% acetic acid (50 ml) and passed through a column of Dowex X1 (acetate form, 2.5×24 cm). The eluate was lyophilized to obtain 2 crude product (2.82 g), which was dissolved in 8 M urea (pH 9.0, 50 ml), and allowed to stand at room temperature for 60 minutes. The solution was charged on a column (2.0×33 cm) of CM-cellulose packed with 8 M urea solution, and eluted by linear gradient elution with 0.01 M ammonium acetate (pH 4.5, 500 ml)—0.3 M ammonium acetate (pH 4.5, 500 ml). The eluate was fractionated into 7.5 ml fractions which were checked by the Folin-Lowry method (500 nm) to obtain fractions Nos 1-22 (fraction $C_1$), fractions Nos. 23-45 (fraction $C_2$), fractions Nos. 46-80 (fraction $C_3$) and fractions Nos. 81-120) fraction $C_4$). Each fraction was passed through a column of Sephadex LH-20 for desalting. Fraction $C_1$ was passed through such a column (3.0×120 cm) to fractionate into 7.5 ml fractions to obtain fractions Nos. 28-42 (fraction $C_1L$). Fraction $C_2$ was passed through such a column (3.4×120 cm) to fractionate it into 7.6 ml fractions to obtain fractions Nos. 33-40 (fraction $C_2L_1$) and Nos. 41-62 (fraction $C_2L_2$). Fraction $C_3$ was passed through such a column (3.0×120 cm), to fractionate it into 6.0 ml fractions to obtain fractions Nos. 31-40 (fraction $C_3L_1$) and Nos.

41-51 (fraction $C_3L_2$). Fraction $C_4$ was passed through such a column (3.4×120 cm) to fractionate it into 7.5 ml fractions to obtain fractions Nos. 35-48 (fraction $C_4L$). Each part was lyophilized to obtain fractions $C_1L$ (312 mg), $C_2L_1$ (142.3 mg), $C_2L_2$ (1380 mg), $C_3L_1$ (104 mg), $C_3L_2$ (510 mg) and $C_4L$ (130 mg).

The above fraction $C_2L_2$ (1380 mg) dissolved in 0.1 N acetic acid (13 ml) was charged on a column (4.3×6.0 cm) of CM-cellulose and eluted by linear gradient elution with 0.01 M ammonium acetate (pH 4.5, 500 ml)—0.1 M ammonium acetate (pH 4.5, 300 ml). The eluate was fractionated into 7.6 ml fractions to obtain fractions Nos. 40-50 (fraction $C_2L_2$-$C_1$) and Nos. 53-77 (fraction $C_2L_2$-$C_2$). Each fraction was passed through Sephadex LH-20 for desalting. Fraction $C_2L_2$-$C_1$ was passed through such a column (2.9×120 cm), and the eluate was fractionated into 8.0 ml fractions to obtain fractions Nos. 26-30 (fraction $C_2L_2$-$C_1L_1$) and Nos. 31-39 (fraction $C_2L_2$-$C_1L_2$). Fraction $C_2L_2$-$C_2$ was passed through such a column (3.4×120 cm) and fractionated into 8 ml fractions to obtain fractions Nos. 34-44 (fraction $C_2L_2$-$C_2L_1$) and Nos. 45-53 (fraction $C_2L_2$-$C_2L_2$). Each fraction was lyophilized to obtain fraction $C_2L_2$-$C_1L_1$ (79 mg), $C_2L_2$-$C_1L_2$ (455 mg), $C_2L_2$-$C_2L_1$ (157.3 mg) and $C_2L_2$-$C_2L_2$ (551.7 mg).

Amino acid analysis of fraction $C_2L_2$-$C_2L_2$: Asp 4.65 (5), Thr 0.97 (1), Ser 3.47 (4), Glu 5.99 (6), Pro 0.93 (1), Gly 1.96 (2), Ala 4 (4), Val 3.97 (4), Leu 3.01 (3), Lys 6.13 (6), His 0.93 (1), Arg 1.96 (2).

Fraction $C_2L_2$-$C_2L_2$ dissolved in 0.1 N acetic acid (5 ml) was charged on a column (4.2×7.0 cm) of CM-cellulose and eluted by linear gradient elution with 0.01 M ammonium acetate (pH 4.5, 300 ml)—0.3 M ammonium acetate (pH 4.5, 300 ml). The eluate was fractionated into 8.0 ml fractions to obtain fractions Nos. 39-45 (fraction $C_2L_2$-$C_2L_2$-C), which was passed through a column (2.9×120 cm) of Sephadex LH-20 for desalting. The eluate was fractionated into 8 ml fractions to obtain fractions Nos. 24-30 (fraction $C_2L_2$-$C_2L_2$-$CL_1$), fractions Nos. 31-35 (fraction $C_2L_2$-$C_2L_2$-$CL_2$) and fractions Nos. 36-39 (fraction $C_2L_2$-$C_2L_2$-$CL_3$). Each fraction was lyophilized to obtain the fraction $C_2L_2$-$C_2L_2$-$CL_2$ (200 mg) and the fraction $C_2L_2$-$C_2L_2$-$CL_1$ (h-PTH [46-84], 94.9 mg).

TLC: $Rf_9$=0.76

Amino acid analysis: Asp 4.86 (5), Thr 0.99 (1), Ser 3.58 (4), Glu 6.17 (6), Pro 0.96 (1), Gly 1.97 (2), Ala 4 (4), Val 4.02 (4), Leu 2.93 (3), Lys 6.05 (6), His 0.90 (1), Arg 1.87 (2).

EXAMPLE 4

[Tyr$^{45}$]H—Pth(45-84);
H—Tyr—Ala—Gly—Ser—Gln—Arg—Pro—Arg—Lys—Lys—Glu—Asp—Asn—Val—Leu—Val—Glu—Ser—His—Glu—Lys—Ser—Leu—Gly—Glu—Ala—Asp—Lys—Ala—Asp—Val—Asp—Val—Leu—Thr—Lys—Ala—Lys—Ser—Gln—Oh (1) P(45-84):
BOC—Tyr(Bzl—$Cl_2$)—Ala—Gly—Ser(Bzl)—Gln—Arg(Tos)—Pro—Arg(Tos)—Lys(Z—Cl)—Lys(Z—Cl)—Glu(OBzl)—Asp(OBzl)—Asn—Val—Leu—Val—Glu(OBzl)—Ser(Bzl)—His—Glu(OBzl)—Lys(Z—Cl)—Ser(Bzl)—Leu—Gly—Glu(OBzl)—Ala—Asp(OBzl)—Lys(Z—Cl)—Ala—Asp(OBzl)—Val—Asp(OBzl)—Val—Leu—Thr(Bzl)—Lys(Z—Cl)—Ala—Lys(Z—Cl)—Ser(Bzl)—Gln—OBzl [47]

TFA (60 ml) was added to substance [46] (6.27 g, 0.9 mM) in Example 3, and the mixture was stirred at room temperature for 60 minutes. The TFA was removed in vacuo and ether was added to residue. The precipitate was filtered to obtain de-BOC compound (6.30 g).

The above de-BOC compound (2.10 g, 03. mM) was dissolved in DMF (35 ml) and NMP (35 ml). BOC—Tyr(Bzl—$Cl_2$)—OH (0.16 g, 1.2 molar excess), HOBT (0.05 g, 1.2 molar excess) and WSCI (0.07 ml, 1.2 molar excess) were added thereto at 0° C., and the mixture was stirred at room temperature overnight. DMF was removed in vacuo and ice water was added to the residue. The precipitate was filtered to obtain substance [47] (2.00 g).

(2) [Tyr$^{45}$]—h—PTH [45-84]

Substance [47] (2.00 g, 0.27 mM) and anisole (1.0 ml) were added to anhydrous HF (20 ml) at 0° C., and stirred for 60 minutes. HF was distilled off in vacuo and ether was added to the residue. The thus-formed precipitate was collected, dissolved in 0.1 N acetic acid (20 ml) and passed through a column of Dowex XI (acetate form, 2.5×15 cm). The eluate was lyophilized to obtain a crude product (1.37 g).

This crude product was dissolved in 8 M urea solution (pH 9.5, 50 ml) and the solution allowed to stand at room temperature for 60 minutes. The solution was charged on a column (4.3×8.0 cm) of CM-cellulose packed with 8 M urea solution, and eluted by linear gradient elution with 0.01 M ammonium acetate (pH 4.5, 400 ml)—0.1 M ammonium acetate (pH 4.5, 400 ml). The eluate was fractionated into 6.5 ml fractions. Each fraction was checked by the Folin-Lowry method (500 nm) to obtain fractions Nos 30-43 (fraction $C_1$), fractions Nos. 51-68 (fraction $C_2$), fractions Nos. 69-83 (fraction $C_3$) and fractions Nos. 84-100 (fraction $C_4$). Each fraction was passed through a column of Sephadex LH-20 for desalting. Fraction $C_1$ was passed through such a column (3.4×120 cm) to fractionate it into 7.5 ml fractions to obtain fractions Nos. 25-41 (fraction $C_1L$). Fraction $C_2$ was passed through such a column (3.0×120 cm) to fractionate it into 7.5 ml fractions to obtain fractions Nos. 25-36 (fraction $C_2L$). Fraction $C_3$ was passed through such a column (2.9×120 cm) to fractionate it into 8.0 ml fractions to obtain fractions Nos. 24-27 (fraction $C_3L_1$) and Nos. 28-38 (fraction $C_3L_2$). Fraction $C_4$ was passed through such a column (2.9–95 cm) to fractionate it into 7.6 ml fractions to obtain fractions Nos. 20-25 (fraction $C_4L_1$) and Nos. 26-30 (fraction $C_4L_2$). Each fraction was lyophilized to obtain fractions $C_1L$ (230.2 mg), $C_3L_1$ (41.8 mg), $C_3L_2$ (222.4 mg), $C_4L_1$ (74.3 mg) and $C_4L_2$ (48.9 mg).

Fraction $C_2L$ hereinabove dissolved in 0.1 N acetic acid (3 ml) was charged on a column (2.1×25 cm) of CM-cellulose, and eluted by linear gradient elution with 0.01 M ammonium acetate solution (pH 4.5, 300 ml)—0.1 M ammonium acetate (pH 4.5, 300 ml). The elute was fractionated into 8.0 ml fractions to obtain fractions Nos. 30-36 (fraction $C_2L$-C) which was passed through a column (2.9×90 cm) of Sephadex LH-20 for desalting. The eluate was fractionated into 8.0 ml fractions and fractions Nos. 20-29 were lyophilized to obtain [Tyr[45]]—h—PTH [45-84] (163.3 mg).

TLC: $Rf_9$=0.75

Amino acid analysis: Asp 4.86 (5), Thr 1.02 (1), Ser 3.51 (4), Glu 6.05 (6), Pro 0.93 (1), Gly 1.90 (2), Ala 4 (4), Val 4.00 (4), Leu 2.93 (3), Tyr 0.88 (1), Lys 6.02 (6), His 0.86 (1), Arg 1.81 (2).

EXAMPLE 5

[Cys(Acm)[45]]—H—PTH (45-84);
H—Cys(Acm)—Ala—Gly—Ser—Gln—Arg—Pro—Arg—Lys—Lys—Glu—Asp—Asn—Val—Leu—Val—Glu—Ser—His—Glu—Lys—Ser—Leu—Gly—Glu—Ala—Asp—Lys—Ala—Asp—Val—Asp—Val—Leu—Thr—Lys—Ala—Lys—Ser—Gln—Oh (1) P(45-84):

BOC—Cys(Acm)—Ala—Gly—Ser(Bzl)—Gln—Arg(Tos)—Pro—Arg(Tos)—Lys(Z—Cl)—Lys(Z—Cl)—Glu(OBzl)—Asp(OBzl)—Asn—Val—Leu—Val—Glu(OBzl)—Ser(Bzl)—His—Glu(OBzl)—Lys(Z—Cl)—Ser(Bzl)—Leu—Gly—Glu(OBzl)—Ala—Asp(OBzl)—Lys(Z—Cl)—Ala—Asp(OBzl)—Val—Asp(OBzl)—Val—Leu—Thr(Bzl)—Lys(Z—Cl)—Ala—Lys(Z—Cl)—Ser(Bzl)—Gln—OBzl [48]

The remaining de-BOC compound (4.20 mg, 0.6 mM) from Example 4 was dissolved in a mixture of DMF (70 ml) and NMP (70 ml). HOBT (0.10 g, 1.2 molar excess), BOC—Cys(Acm)—OH (0.20 g, 1.02 molar excess) and WSCI (0.13 ml, 1.2 molar excess) were added at 0° C. thereto, and the mixture was stirred at room temperature overnight. The DMF was distilled off in vacuo, ice water was added to the residue and the precipitate was collected. The precipitate was suspended in ethanol, heated, and thereafter cooled, and the insoluble material was collected by filtration. This operation was twice repeated to obtain substance [48] (4.07 g, yield: 95.0%).

(2) [Cys(Acm)[45]] h-PTH [45-84]

Substance [48] (4.00 g, 0.57 mM) and anisole (10 ml) were added at 0° C. to anhydrous HF (60 ml), and the mixture was stirred for 60 minutes. The HF was distilled off in vacuo and ether was added to the residue. The precipitate was dissolved in 20% acetic acid (40 ml) and passed through a column of Dowex X1 (acetate form, 2.8×35 cm). The lyophilized eluate was dissolved in 8 M urea solution, adjusted to pH 9.0 by adding aqueous ammonia, the allowed to stand for 30 minutes. The solution was charged on a column (3.4×35 cm) of CM-cellulose packed with 8 M urea solution and eluted by linear gradient elution with 0.01 M ammonium acetate (pH 4.5, 700 ml)—0.3 M ammonium acetate (pH 4.5, 700 ml). The eluate was fractionated into 8 ml fractions and checked by the Folin-Lowry method (500 nm) to obtain fractions Nos 25-35 (fraction $C_1$), fractions Nos. 36-45 (fraction $C_2$) and fractions Nos. 46-84 (fraction $C_3$). Each fraction was passed through Sephadex LH-20 for desalting. Fraction $C_2$ was passed through such a column (3.0×120 cm) and fractionated into 8.0 ml fractions to obtain fractions Nos. 27-33 (fraction $C_2L_1$) and Nos. 34-40 (fraction $C_2L_2$). Fraction $C_3$ was passed through such a column (3.4×120 cm), and fractionated into 8.0 ml fractions to obtain fractions Nos. 35-47 (fraction $C_3L_1$) and Nos. 48-53 (fraction $C_3L_2$). Each fraction was lyophilized to obtain fractions $C_2L_1$ (148 mg), $C_2L_2$ (620 mg), $C_3L_1$ (212 mg) and $C_3L_2$ (605 mg).

The above fraction $C_2L_2$ dissolved in 0.1 N acetic acid (6 ml) was charged on a column (5.0×12 cm) of CM-cellulose and eluted by linear gradient elution with 0.01 M ammonium acetate (pH 4.5, 400 ml)—0.3 M ammonium acetate (pH 4.5, 400 ml). The eluate was fractionated into 6.0 ml fractions to obtain fractions Nos. 110-126 (fraction $C_2L_2$-C), which was passed through a column (4.0×120 cm) of Sephadex LH-20 for desalting. The eluate was fractionated into 8 ml fractions. Fractions Nos. 38-54 (fraction $C_2L_2$-CL) was lyophilized to obtain [Cys(Acm)[45]] h-PTH [45-84] (246.8 mg).

TLC: $Rf_9$=0.74

Amino acid analysis: Asp 4.91 (5), Thr 0.98 (1), Ser 3.50 (4), Glu 6.11 (6), Pro 0.98 (1), Gly 1.98 (2), Ala 4 (4), Val 4.04 (4), Cys 0.42 (0.5), Leu 2.90 (3), Lys 5.99 (6), His 0.87 (1), Arg 1.87 (2).

EXAMPLE 6

[Cys[45]]—H—PTH (45-84);
H—Cys—Ala—Gly—Ser—Gln—Arg—Pro—Arg—Lys—Lys—Glu—Asp—Asn—Val—Leu—Val—Glu—Ser—His—Glu—Lys—Ser—Leu—Gly—Glu—Ala—Asp—Lys—Ala—Asp—Val—Asp—Val—Leu—Thr—Lys—Ala—Lys—Ser—Gln—Oh

[Cys(Acm)[45]] h-PTH [45-84] (88 mg, 0.02 mM) obtained in Example 5 was dissolved in 50% acetic acid (2 ml). Mercuric acetate (52.24 mg, 0.18 mM) was added thereto, and the mixture was stirred at room temperature for 70 minutes. β-Mercaptoethanol (3.4 ml) was added, and the mixture was stirred at room temperature for 24 hours. The reaction mixture was centrifuged and the supernatant solution was charged on a column (3.2×42 cm) of Sephadex LH-20 and eluted with 0.1 M acetic acid. The eluate was fractionated into 5 ml fractions and the ninhydrin-positive fractions Nos. 9–14 were collected and lyophilized to obtain [Cys[45]] h-PTH [45-84] (76.1 mg).

TLC: $Rf_9$=0.73

EXAMPLE 7

[Tyr[52]]H—PTH (52-84);
H—Tyr—Lys—Lys—Glu—Asp—Asn—Val—Leu—Val—Glu—Ser—His—Glu—Lys—Ser—Leu—Gly—Glu—Ala—Asp—Lys—Ala—Asp—Val—Asp—Val—Leu—Thr—Lys—Ala—Lys—Ser—Gln—Oh (1) P(52-84):

BOC—Tyr(Bzl—$Cl_2$)—Lys(Z—Cl)—Lys(Z—Cl)—Glu(OBzl)—Asp(OBzl)—Asn—Val—Leu—Val—Glu(OBzl)—Ser(OBzl)—His—Glu(OBzl)—Lys(Z—Cl)—Ser(Bzl)—Leu—Gly—Glu(OBzl)—Ala—Asp(OBzl)—Lys(Z—Cl)—Ala—Asp(OBzl)—Val—Asp(OBzl)—Val—Leu—Thr(Bzl)—Lys(Z—Cl)—Ala—Lys(Z—Cl)—Ser(Bzl)—Gln—OBzl [49]

TFA (50 ml) was added to substance [35] (5.82 g, 1.0 mM) obtained in Example 1 and the mixture was stirred at room temperature for 50 minutes. The TFA was removed off in vacuo, and ether was added thereto. The precipitate was dissolved in DMF (150 ml) and NMP (150 ml). HOBT (0.27 g, 2 molar excess) was added thereto to dissolve the same, then WSCI (0.37 ml, 2 molar excess was added), and the mixture was stirred at room temperature for two days. The reaction mixture was poured into ice water, and the precipitate was collected, washed with water, suspended in methanol, heated and cooled. The insoluble materials were collected by filtration. The precipitate was suspended in methanol, and heated. This suspension was cooled and the precipitate collected to obtain substance [49] (5.59 g, yield: 91.0%).

Amino acid analysis: Asp 4.09 (5), Thr 0.90 (1), Ser 1.65 (3), Glu 4.10 (5), Gly 0.88 (1), Ala 3 (3), Val 3.41 (4), Leu 2.50 (3), Tyr 0.82 (1), Lys 5.40 (6), His 0.71 (1).

(2) [Tyr$^{52}$] h-PTH [52-84]

Substance [49] (3.68 g, 0.6 mM) and anisole (5 ml) were added to anhydrous HF (50 ml) at 0° C., and the mixture was stirred for 60 minutes. The HF was distilled off in vacuo and ether was added to the residue. The precipitate was collected and dissolved in 0.1 N acetic acid (50 ml). The solution was passed through a column of Dowex X1 (acetate form, 2×45 cm), then eluted with 0.1 N acetic acid. The eluate was lyophilized to obtain a crude material (2.30 g), which was dissolved in 8 M urea solution (50 ml), adjusted to pH 9.5 by adding aqueous ammonia, then allowed to stand at 0° C. for 60 minutes. This solution was charged on a column (4.4×12 cm) of CM-cellulose packed with 8 M urea solution, and eluted with 0.01 M ammonium acetate (pH 4.5, about 100 ml), thereafter eluted by linear gradient elution with 0.01 M ammonium acetate (pH 4.5, 700 ml)—0.1 M ammonium acetate (pH 4.5, 700 ml), then eluted with 0.2 M ammonium actate (300 ml). The eluate was fractionated into 13.5 fractions, which were checked by absorbency at UV 280 nm to collect fractions Nos. 54-110, which were lyophilized. The lyophilizate dissolved in 0.1 N acetic acid (5 ml) was passed through a Sephadex LH-20 column (3.4×120 cm). The eluate was fractionated into 8.5 ml fractions, and fractions Nos. 47-53 were collected and lyophilized to obtain a material (510 mg). This material was dissolved in 0.1 N acetic acid (20 ml) and charged on a column (4.5×70 cm) of CM-cellulose which was eluted by linear gradient elution with 0.01 M ammonium acetate (pH 4.5, 500 ml)—0.1 M ammonium acetate (pH 4.5, 500 ml). The eluate was fractionated into 6.0 ml fractions. Each fraction was checked by absorbency of UV at 280 nm and fractions Nos. 109-120 were collected and lyophilized. The lyophilizate was dissolved in 0.1 N acetic acid (5 ml) which was passed through a column (3.4×120 cm) of Sephadex LH-20. The eluate was withdrawn as 3.4 ml fractions, and fractions Nos. 56-73 were collected and lyophilized to obtain [Tyr$^{52}$] h-PTH [52-84] (102 mg).

TLC: $Rf_9$=0.75, one spot

Amino acid analysis: Asp 4.55 (5), Thr 0.93 (1), Ser 2.20 (3), Glu 4.98 (5), Gly 0.96 (1), Ala 3, Val 3.98 (4), Leu 2.93 (3), Tyr 0.90 (1), Lys 6.10 (6), His 1.00 (1).

EXAMPLE 8

[Tyr$^{50}$] H—PTH (50-84);
H—Tyr—Pro—Arg—Lys—Glu—Asp—Asn—Val—Leu—Val—Glu—Ser—His—Glu—Lys—Ser—Leu—Gly—Glu—Ala—Asp—Lys—Ala—Asp—Val—Asp—Val—Leu—Thr—Lys—Ala—Lys—Ser—Gln—Oh (1) P(50-84):
BOC—Tyr(Bzl—$Cl_2$)—Pro—Arg(Tos)—Lys(Z—Cl)—Lys(Z—Cl)—Glu(OBzl)—Asp(OBzl)—Asn—Val—Leu—Val—Glu(OBzl)—Ser(Bzl)—His—Glu(OBzl)—Lys(Z—Cl)—Ser(Bzl)—Leu—Gly—Glu(OBzl)—Ala—Asp(OBzl)—Lys(Z—Cl)—Ala—Asp(OBzl)—Val—Asp(OBzl)—Val—Leu—Thr(Bzl)—Lys(Z—Cl)—Ala—Lys(Z—Cl)—Ser(Bzl)—Gln—OBzl [50]

TFA (50 ml) was added to substance [39] in Example 2 and the mixture was stirred at room temperature for 55 minutes. The TFA was distilled off in vacuo and ether was added thereto. The thus-formed precipitate was dissolved in DMF (160 ml) and NMP (160 ml). HOBT (0.27 g, 2 molar excess) and BOC—Tyr(Bzl—$Cl_2$)—OH (0.88 g, 2 molar excess) were added to dissolve the same, and the solution was cooled to −20° C. WSCI (0.37 ml, 2 molar excess) was added and the mixture was stirred at room temperature for three days. The reaction mixture was poured into ice water. The precipitate thus formed was collected, washed with water, suspended in methanol, and heated. Thereafter the methanol suspension was cooled and the insoluble materials were filtered off. The precipitate was again suspended with heating in methanol, and cooled to collect the precipitate. This operation was repeated again, and the precipitate was washed with ether to obtain substance [50] (2.00 g, yield: 90%).

Amino acid analysis: Asp 4.21 (5), Thr 0.95 (1), Ser 2.32 (3), Glu 4.50 (5), Pro 0.75 (1), Gly 0.88 (1), Ala 3, Val 3.45 (4), Leu 2.60 (3), Tyr 0.70 (1), Lys 5.21 (6), His 0.72 (1), Arg 0.71 (1).

(2) [Tyr$^{50}$] h-PTH [50-84]

Substance [50] (3.98 g, 0.6 mM) and anisole (6 ml) were added to anhydrous HF (60 ml) at 0° C., and the mixture was stirred at 0° C. for 60 minutes. The HF was distilled off in vacuo, ether was added to the residue and the precipitate was collected and dissolved in 0.1 N acetic acid (50 ml) and passed through a column of Dowex X1 (acetate form, 3×45 cm). The eluate was lyophilized to obtain a crude product (2.30 g). This was dissolved in 8 M urea solution, which was adjusted to pH 10.0 by adding aqueous ammonia, and allowed to stand at 0° C. for 30 minutes. The solution was charged on a column (4.2×11.5 cm) of CM-cellulose packed with 8 M urea solution, and eluted with 0.01 M ammonium acetate solution (pH 4.5) to remove the urea, thereafter eluted by linear gradient elution with 0.01 M ammonium acetate (pH 4.5, 700 ml)—0.1 M ammonium acetate (pH 4.5, 700 ml), then eluted with 0.2 M ammonium acetate solution (pH 4.5, 250 ml). The eluate was fractionated into 8.5 fractions, which were checked by absorbency at 280 nm, then fractions Nos. 110-155 were collected and lyophilized. The lyophilizate dissolved in 0.01 M acetic acid (6 ml) was passed through a column of Sephadex LH-20 (3.4×110 cm). Fractions Nos. 66-82, each of 5.2 ml, were collected and lyophilized to obtain the lyophilizate (360 mg). This lyophilizate was dissolved in 0.1 N acetic acid (10 ml), charged on a column (2.0×31 cm) of CM-cellulose, and eluted by linear gradient elution with 0.01 M ammonium acetate (pH 4.5, 500 ml)—0.2 M ammonium acetate (pH 4.5, 500 ml). The eluate was fractionated into 7.5 ml fractions. Fractions Nos. 90-100 were collected, lyophilized and dissolved in 0.1 N acetic acid (3 ml). The solution was passed through a column (3.0×123 cm) of Sephadex LH-20. The eluate was fractionated into 6 ml fractions, and fractions Nos. 35-43 were collected and lyophilized to obtain [Tyr[50]] h-PTH [52-84] (115 mg).

TLC: $Rf_{10}=0.88$ (one spot)

Amino acid analysis: Asp 4.95 (5), Thr 0.91 (1), Ser 2.32 (3), Glu 5.10 (5), Pro 1.01 (1), Gly 0.99 (1), Ala 3, Val 4.01 (4), Leu 2.99 (3), Tyr 0.85 (1), Lys 6.03 (6), His 0.92 (1), Arg 1.02 (1).

EXAMPLE 9

(1) Antigens h-PTH [53-842, h-PTH [51-84], h-PTH [46-84] and BSA-[Cys[45]] h-PTH [45-84] obtained by the method hereinbelow were used as antigens.

BSA-[Cys[45]] h-PTH [45-84] was prepared as follows: Tetrasodium EDTA (4 mg) was added to BSA (50 mg) dissolved in 0.1 M phosphate buffer (pH 8.0, 1 ml). Dimethylformamide solution (150 μl) of 3-(2'-benzothiazolyl-dithio) propionate succinimide ester (500 μg) was added thereto and the mixture was stirred with ice cooling for 60 minutes. After reaction, [Cys[45]] h-PTH [45-84] (50 mg) was added thereto, and the reaction proceeded with ice cooling for 30 minutes, after which the pH was adjusted to 7.0, and the material was passed through a column (1×50 cm) of Sephadex G-75 packed with 0.01 M phosphate buffer (pH 7.2) containing 0.15 M NaCl, for gel filtration. Eluates of 15 ml-20 ml were collected to obtain the fractions containing BSA-[Cys[45]] h-PTH [45-84]. [On the average, 11 moles of [Cys[45]] h-PTH [45-84] was conjugated per one mole of BSA.]

(2) Antibodies

A solution (500 μg/ml) of the above antigen in 0.01 M phosphate buffer (pH 7.0) containing 0.15 M NaCl was prepared. Each 2.5 ml of this solution was mixed with Freund's complete adjuvant (2.5 ml), and used to immunize male guinea pigs, five in each group, by injecting subcutaneously (subcutaneous injection five times at two-week intervals). Two weeks after the final immunization, blood was collected from the heart to obtain the antiserum by a conventional method.

In the following, antiserum of h-PTH [53-84] is abbreviated as (A); antiserum of h-PTH [51-84] is abbreviated as (B); antiserum of h-PTH [46-84] is abbreviated as (C); and antiserum of BSA-[Cys[45]] h-PTH [45-84] is abbreviated as (D).

(3) Enzyme-labelling (1) [Cys[45]] h-PTH [45-84] (4 mg) was dissolved in 0.1 M phosphate buffer (pH 7.0, 1 ml). N-[2-(2'-pyridyldithio)ethyl]-3-(2-benzothiazolyl-dithio)propionamide (0.6 mg) in dimethylformamide (0.9 ml) was added thereto, and the mixture was stirred at 0° C. for 60 minutes. The pH was adjusted to pH 6.0 by adding HCl. The solution was passed through a Sephadex G-25 column (1×50 cm) packed with 0.1 M phosphate buffer (pH 6.0) to obtain one-milliliter fractions of which fractions 15-19 were collected (660 γ/ml of [Cys[45]] h-PTH [45-84]). 20 μl of the collected material was added to 0.1 M phosphate buffer (pH 8.0, 1.5 ml) containing β-galactosidase (1.2 mg), and the mixture was stirred at 0° C. for 60 minutes. The incubation mixture was passed through a Sephadex G-100 column (1×50 cm) packed with 0.01 M phosphate buffer (pH 7.2) containing 0.15 M NaCl for gel filtration to obtain one-milliliter fractions of which fractions 13-17 were collected. In this collected material, the ratio of β-galactosidase labelled conjugate to [Cys[45]] h-PTH [45-84] is about 1:1 (hereinafter designated as Lot A).

(2) h-PTH [53-84] (2 mg) was dissolved in 0.1 M phosphate buffer (pH 8.0, 1 ml). Dimethylformamaide solution (0.2 ml) of 3-(2'-benzothiazolyl-dithio) propionate succinimide ester (0.2 mg) was added thereto, and the mixture was stirred at 0° C. for 60 mins. After reaction, 20 μl thereof was added to 0.1 M phosphate buffer (pH 7.0, 1 ml) containing β-galactosidase (1 mg), and the mixture reacted at 0° C. for 60 minutes. The reaction mixture was passed through a Sephadex G-100 column (1×50 cm) for gel filtration to obtain one-milliliter fractions of which fractions 14-17 were collected. The ratio of β-galactosidase conjugate is h-PTH [53-84]: β-galactosidase=1:1 (hereinafter designated as Lot B).

(4) Assay method

Specimen solution (100 μl), enzyme-labelled conjugate (100 μl), aliquot-dilution antiserum (100 μl) and normal guinea pig serum (100-fold dilution) (100 μl) were incubated at 5° C. for 24 hours. Anti-guinea pig γ-globulin rabbit serum (10-fold dilution, 100 μl) was added thereto and the mixture was incubated at 5° C. for 24 hours. 0.5 M NaCl (3 ml) was added thereto and the mixture was centrifuged at 3000 r.p.m. for 15 minutes to collect the sedimentate. The sedimentate was added to 0.1 M phosphate buffer (containing 0.1% sodium azide, 0.1% BSA, 20 mM mercaptoethanol and 10% ethanol, pH 6.7) containing o-nitrophenyl-β-galactoside (5 mg/ml) (200 μl), and the mixture was reacted at 37° C. for 90 minutes. The reaction was stopped by adding 0.2 M glycine buffer (pH 10.4, 2.5 ml) and the material was measured optically at 420 nm.

0.01 M phosphate buffer (pH 7.2) containing 0.1% sodium azide, 0.25% BSA, 0.15 M NaCl and 5 mM EDTA, was used as dilution medium.

(1) Lot A was used as enzyme-labelled conjugate. The antibody titer (Bo/T) of each antiserum hereinabove was assayed. The results are shown in Table 3. Each antiserum was used in 1000-fold dilution.

TABLE 3

| Antiserum | Guinea Pig No. | Antibody Titer $\left(\frac{Bo}{T}\right)\%$ |
|---|---|---|
| A | A-1 | 19 |
| | A-2 | 23 |
| | A-3 | 17 |
| B | B-1 | 15 |
| | B-2 | 16 |
| | B-3 | 16 |
| C | C-1 | 38 |
| | C-2 | 39 |
| | C-3 | 34 |
| D | D-1 | 30 |
| | D-2 | 46 |
| | D-3 | 42 |

(2) Enzyme-labelled conjugate Lot B was used and the antibody titer (Bo/T) was assayed on the above C and D antisera.

TABLE 4

| Antiserum | Guinea Pig No. | Antibody Titer $\left(\frac{Bo}{T}\right)\%$ |
|---|---|---|
| C | C-1 | 29 |
| | C-2 | 32 |
| | C-3 | 29 |
| D | D-1 | 24 |

TABLE 4-continued

| Antiserum | Guinea Pig No. | Antibody Titer $\left(\frac{Bo}{T}\right)\%$ |
|---|---|---|
| | D-2 | 34 |
| | D-3 | 34 |

Each antiserum was used in 2000-fold dilution.

(3) Standard curves were prepared by using the antisera hereinabove.

Antisera used: A-2, 600-fold dilution; B-2, 500-fold dilution; C-2, 1500-fold dilution; and D-2, 2000-fold dilution.

Enzyme-labelled conjugate: Lot B.

The standard curve of h-PTH [53-84] was prepared using the aboves.

The results are shown in the accompanying drawings, in which.

Figure 1:
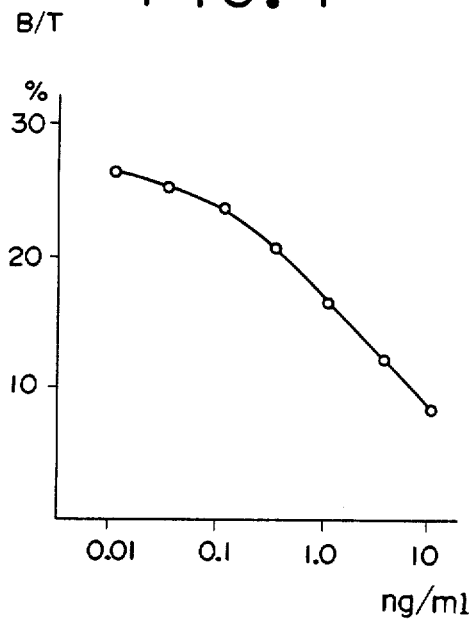
FIG. 1 is the standard curve for A-2.
Figure 2:
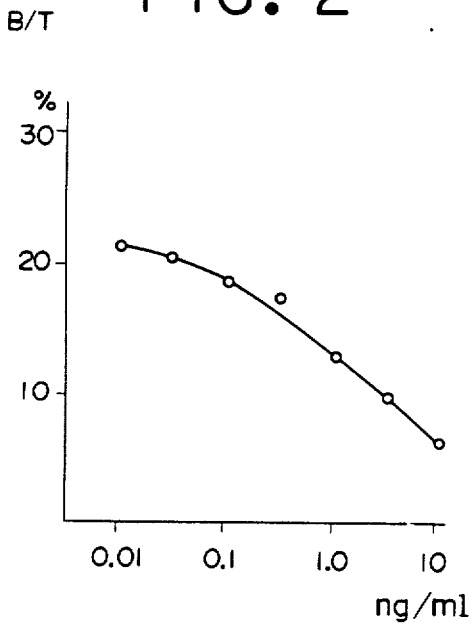
FIG. 2 is the standard curve for B-2.
Figure 3:
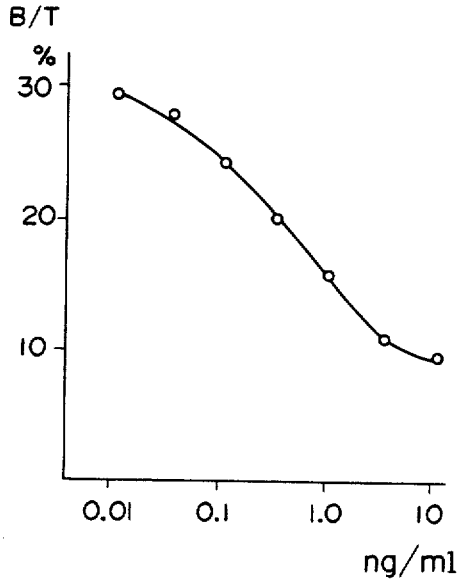
FIG. 3 is the standard curve for C-2.
Figure 4:
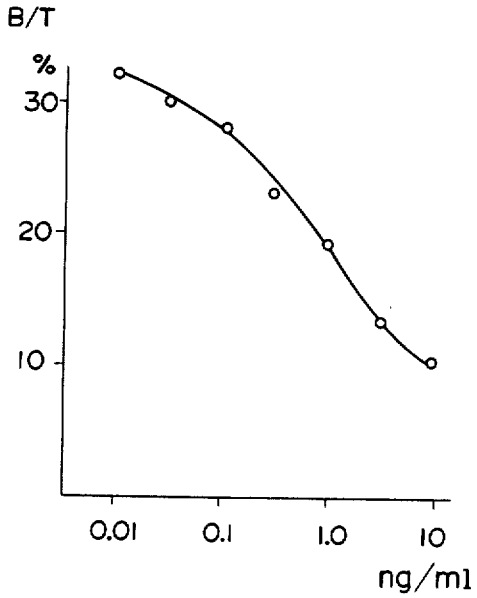
FIG. 4 is the standard curve for D-2.

As shown by the above, antisera obtained by using peptide [Ia] of the present invention provide desirable standard curves; and hence h-PTH or its C-terminal fragments can be assayed by EIA with good accuracy.

What is claimed is:

1. A peptide of the formula

R—Lys—Lys—Glu—Asp—Asn—Val—Leu—Val—Glu—Ser—His—Glu—Lys—Ser—Leu—Gly—Glu—Ala—Asp—Lys—Ala—Asp—Val—Asp—Val—Leu—Thr—Lys—Ala—Lys—Ser—Gln—OH [I]

wherein R is [H,] H—Tyr— or $R_1$—Pro—Arg—, $R_1$ is H, H—Tyr— or $R_2$—Ala—Gly—Ser—Gln—Arg—, and $R_2$ is H, H—Cys— or H—Tyr—, or a salt thereof.

* * * * *